(12) United States Patent
Tanaka et al.

(10) Patent No.: US 12,135,432 B2
(45) Date of Patent: *Nov. 5, 2024

(54) SYSTEM AND METHOD DIRECTED TO AN EYEGLASSES-TYPE WEARABLE DEVICE

(71) Applicant: KABUSHIKI KAISHA TOSHIBA, Tokyo (JP)

(72) Inventors: Akira Tanaka, Tokyo (JP); Yasuhiro Kanishima, Tokyo (JP); Kenichi Doniwa, Asaka Saitama (JP); Hiroaki Komaki, Tokyo (JP); Hiroki Kumagai, Tokyo (JP); Takashi Sudo, Tokyo (JP); Nobuhide Okabayashi, Tokyo (JP)

(73) Assignee: KBUSHIKI KAISHA TOSHIBA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/451,535

(22) Filed: Aug. 17, 2023

(65) Prior Publication Data

US 2023/0384603 A1    Nov. 30, 2023

Related U.S. Application Data

(60) Continuation of application No. 17/897,968, filed on Aug. 29, 2022, now Pat. No. 11,789,279, which is a
(Continued)

(30) Foreign Application Priority Data

Sep. 1, 2015   (JP) .................................. 2015-171933

(51) Int. Cl.
*G02B 27/01*      (2006.01)
*G02B 27/00*      (2006.01)
(Continued)

(52) U.S. Cl.
CPC ....... *G02B 27/0179* (2013.01); *G02B 27/017* (2013.01); *G06F 1/163* (2013.01);
(Continued)

(58) Field of Classification Search
None
See application file for complete search history.

(56) References Cited

U.S. PATENT DOCUMENTS 6,452,544 B1    9/2002  Hakala et al.
6,600,461 B1    7/2003  Okauchi et al.
(Continued)

FOREIGN PATENT DOCUMENTS

JP      H04-88312 A     3/1992
JP      H05-211650 A    8/1993
(Continued)

OTHER PUBLICATIONS

U.S. Appl. No. 14/979,169, filed Dec. 22, 2015 Advisory Action dated Dec. 22, 2017.
(Continued)

*Primary Examiner* — Jeffrey J Chow
(74) *Attorney, Agent, or Firm* — Rutan & Tucker, LLP

(57) ABSTRACT

According to one embodiment, a system includes a wearable device configured to be attached to a display configured to display a display image. The wearable device features an optical component set featuring a lens, a first user operable member configured to set an adjustment value relating to a projection angle of the visual image, and a second user operable member configured to set an adjustment value relating to at least one of a color tone or a brightness of the visual image. A position of the visual image is changed by adjusting the projection angle of the visual image using the first user operable member so that the visual image is displayed at a position based on at least one of a shape or a
(Continued)

size of the head of the user. The color tone or the brightness of the visual image is changed using the second user operable member.

5 Claims, 13 Drawing Sheets

Related U.S. Application Data continuation of application No. 17/210,420, filed on Mar. 23, 2021, now Pat. No. 11,428,944, which is a continuation of application No. 16/851,088, filed on Apr. 16, 2020, now Pat. No. 11,002,975, which is a division of application No. 15/685,766, filed on Aug. 24, 2017, now abandoned, which is a division of application No. 14/979,169, filed on Dec. 22, 2015, now Pat. No. 10,685,232.

(51) Int. Cl.

| | | |
|---|---|---|
| *G06F 1/16* | (2006.01) | |
| *G06F 3/01* | (2006.01) | |
| *G06F 3/0346* | (2013.01) | |
| *G06V 20/20* | (2022.01) | |
| *A61K 9/19* | (2006.01) | |
| *A61K 39/00* | (2006.01) | |
| *A61K 39/12* | (2006.01) | |
| *B65B 3/00* | (2006.01) | |
| *C12N 7/00* | (2006.01) | |

(52) U.S. Cl.
CPC ............ *G06F 1/169* (2013.01); *G06F 1/1694* (2013.01); *G06V 20/20* (2022.01); *A61K 9/19* (2013.01); *A61K 39/12* (2013.01); *A61K 2039/5254* (2013.01); *A61K 2039/70* (2013.01); *B65B 3/003* (2013.01); *C12N 7/00* (2013.01); *C12N 2770/24134* (2013.01); *C12N 2770/24151* (2013.01); *C12N 2770/24164* (2013.01); *G02B 27/0093* (2013.01); *G02B 2027/0138* (2013.01); *G02B 2027/014* (2013.01); *G02B 2027/0178* (2013.01); *G02B 2027/0187* (2013.01); *G06F 3/011* (2013.01); *G06F 3/012* (2013.01); *G06F 3/0346* (2013.01); *Y02A 50/30* (2018.01)

(56) References Cited

U.S. PATENT DOCUMENTS

| | | |
|---|---|---|
| D748,203 S | 1/2016 | Karunaratne |
| 10,671,849 B2 | 6/2020 | Tanaka et al. |
| 10,682,405 B2 | 6/2020 | Tanaka et al. |
| 10,685,232 B2 | 6/2020 | Tanaka et al. |
| 11,428,944 B2 | 8/2022 | Tanaka et al. |
| 2005/0073423 A1 | 4/2005 | Kim |
| 2006/0119539 A1 | 6/2006 | Kato et al. |
| 2006/0227779 A1 | 10/2006 | Shimizu |
| 2007/0097324 A1 | 5/2007 | Kikuchi et al. |
| 2007/0296646 A1 | 12/2007 | Yamamoto et al. |
| 2008/0297360 A1 | 12/2008 | Knox et al. |
| 2010/0070456 A1 | 3/2010 | Sugihara et al. |
| 2010/0194782 A1 | 8/2010 | Gyorfi et al. |
| 2010/0214635 A1 | 8/2010 | Sasaki et al. |
| 2011/0221656 A1 | 9/2011 | Haddick et al. |
| 2011/0239354 A1* | 10/2011 | Celona ................... A42B 3/04 2/422 |
| 2012/0242560 A1 | 9/2012 | Nakada et al. |
| 2013/0120449 A1 | 5/2013 | Ihara et al. |
| 2013/0127980 A1 | 5/2013 | Haddick et al. |
| 2013/0214998 A1 | 8/2013 | Andes et al. |
| 2013/0217294 A1 | 8/2013 | Karunaratne |
| 2013/0217295 A1 | 8/2013 | Karunaratne |
| 2014/0085203 A1 | 3/2014 | Kobayashi |
| 2014/0145079 A1 | 5/2014 | Omino |
| 2014/0172432 A1 | 6/2014 | Sendai |
| 2014/0204021 A1* | 7/2014 | Sugihara ................ G06F 3/013 345/156 |
| 2014/0206133 A1 | 7/2014 | Koezuka et al. |
| 2014/0240349 A1 | 8/2014 | Tuukkanen |
| 2014/0240484 A1 | 8/2014 | Kodama et al. |
| 2014/0250153 A1 | 9/2014 | Nixon et al. |
| 2014/0273847 A1 | 9/2014 | Nixon et al. |
| 2014/0274123 A1 | 9/2014 | Nixon et al. |
| 2014/0277593 A1 | 9/2014 | Nixon et al. |
| 2014/0277594 A1 | 9/2014 | Nixon et al. |
| 2014/0277595 A1 | 9/2014 | Nixon et al. |
| 2014/0277596 A1 | 9/2014 | Nixon et al. |
| 2014/0277604 A1 | 9/2014 | Nixon et al. |
| 2014/0277605 A1 | 9/2014 | Nixon et al. |
| 2014/0277607 A1 | 9/2014 | Nixon et al. |
| 2014/0277615 A1 | 9/2014 | Nixon et al. |
| 2014/0277616 A1 | 9/2014 | Nixon et al. |
| 2014/0277617 A1 | 9/2014 | Nixon et al. |
| 2014/0277618 A1 | 9/2014 | Nixon et al. |
| 2014/0277656 A1 | 9/2014 | Nixon et al. |
| 2014/0278312 A1 | 9/2014 | Nixon et al. |
| 2014/0280497 A1 | 9/2014 | Nixon et al. |
| 2014/0280678 A1 | 9/2014 | Nixon et al. |
| 2014/0282015 A1 | 9/2014 | Nixon et al. |
| 2014/0282227 A1 | 9/2014 | Nixon et al. |
| 2014/0282257 A1 | 9/2014 | Nixon et al. |
| 2014/0351191 A1 | 11/2014 | Kon et al. |
| 2014/0361957 A1 | 12/2014 | Hua et al. |
| 2015/0015461 A1 | 1/2015 | Morimoto |
| 2015/0029341 A1 | 1/2015 | Sinha |
| 2015/0051008 A1 | 2/2015 | Schmok |
| 2015/0062164 A1 | 3/2015 | Kobayashi et al. |
| 2015/0154598 A1 | 6/2015 | Forte et al. |
| 2015/0199062 A1 | 7/2015 | Lang |
| 2015/0220080 A1 | 8/2015 | Nixon et al. |
| 2015/0260993 A1 | 9/2015 | Bickerstaff et al. |
| 2015/0261215 A1 | 9/2015 | Blevins et al. |
| 2015/0323798 A1* | 11/2015 | Huang ................ G02B 27/017 359/632 |
| 2016/0043866 A1 | 2/2016 | Nixon et al. |
| 2016/0055692 A1 | 2/2016 | Trani |
| 2016/0098021 A1 | 4/2016 | Zornio et al. |
| 2016/0098037 A1 | 4/2016 | Zornio et al. |
| 2016/0098388 A1 | 4/2016 | Blevins et al. |
| 2016/0098647 A1 | 4/2016 | Nixon et al. |
| 2016/0132046 A1 | 5/2016 | Beoughter et al. |
| 2016/0140868 A1 | 5/2016 | Lovett et al. |
| 2016/0178912 A1 | 6/2016 | Kusuda et al. |
| 2016/0253019 A1 | 9/2016 | Geaghan |
| 2016/0343168 A1 | 11/2016 | Mullins et al. |
| 2016/0361662 A1 | 12/2016 | Karunaratne |
| 2017/0024612 A1 | 1/2017 | Wexler et al. |
| 2017/0059869 A1 | 3/2017 | Lee |
| 2017/0061212 A1 | 3/2017 | Tanaka et al. |
| 2017/0094257 A1 | 3/2017 | Zhang et al. |
| 2017/0102678 A1 | 4/2017 | Nixon et al. |
| 2017/0102693 A1 | 4/2017 | Kidd et al. |
| 2017/0102694 A1 | 4/2017 | Enver et al. |
| 2017/0102696 A1 | 4/2017 | Bell et al. |
| 2017/0103103 A1 | 4/2017 | Nixon et al. |
| 2017/0132554 A1 | 5/2017 | Oonishi et al. |
| 2017/0227779 A1 | 8/2017 | Kato et al. |
| 2017/0235152 A1 | 8/2017 | Border |
| 2017/0351919 A1 | 12/2017 | Tanaka et al. |
| 2017/0351920 A1 | 12/2017 | Tanaka et al. |
| 2017/0351921 A1 | 12/2017 | Tanaka et al. |
| 2018/0024369 A1 | 1/2018 | Kato |
| 2018/0025519 A1 | 1/2018 | Asayama et al. |
| 2018/0031847 A1 | 2/2018 | Tatsuta et al. |
| 2018/0098058 A1 | 4/2018 | Cichonski |
| 2020/0030434 A1 | 1/2020 | Tanaka et al. |
| 2020/0034625 A1 | 1/2020 | Tanaka et al. |

(56) References Cited

U.S. PATENT DOCUMENTS

| | | |
|---|---|---|
| 2020/0293780 A1 | 9/2020 | Tanaka et al. |
| 2021/0208410 A1 | 7/2021 | Tanaka et al. |

FOREIGN PATENT DOCUMENTS

| | | | |
|---|---|---|---|
| JP | H07-93020 | A | 4/1995 |
| JP | H7-121119 | A | 5/1995 |
| JP | H10-147411 | A | 6/1998 |
| JP | H10-198289 | A | 7/1998 |
| JP | 2000-354943 | A | 12/2000 |
| JP | 2002-162597 | A | 6/2002 |
| JP | 2002-288294 | A | 10/2002 |
| JP | 2003-196681 | A | 7/2003 |
| JP | 2003-216687 | A | 7/2003 |
| JP | 2004-101197 | A | 4/2004 |
| JP | 2004-102727 | A | 4/2004 |
| JP | 2005-250990 | A | 9/2005 |
| JP | 2006-3157 | A | 1/2006 |
| JP | 2006-146803 | A | 6/2006 |
| JP | 2006-209144 | A | 8/2006 |
| JP | 2007-121600 | A | 5/2007 |
| JP | 2007-336166 | A | 12/2007 |
| JP | 2008-33891 | A | 2/2008 |
| JP | 2008-201569 | A | 9/2008 |
| JP | 2009-257890 | A | 11/2009 |
| JP | 2009-279193 | A | 12/2009 |
| JP | 2010-72811 | A | 4/2010 |
| JP | 2010-271928 | A | 12/2010 |
| JP | 2010-272041 | A | 12/2010 |
| JP | 2011-081737 | A | 4/2011 |
| JP | 2011-118683 | A | 6/2011 |
| JP | 2011-164631 | A | 8/2011 |
| JP | 2011-248860 | A | 12/2011 |
| JP | 2012-8290 | A | 1/2012 |
| JP | 2012-63638 | A | 3/2012 |
| JP | 2012-212991 | A | 11/2012 |
| JP | 2012-233986 | A | 11/2012 |
| JP | 2013-020422 | A | 1/2013 |
| JP | 2013-195924 | A | 9/2013 |
| JP | 2014-66927 | A | 4/2014 |
| JP | 2014-137522 | A | 7/2014 |
| JP | 2014-145734 | A | 8/2014 |
| JP | 2014-164482 | A | 9/2014 |
| JP | 2014-199349 | A | 10/2014 |
| JP | 2014-199918 | A | 10/2014 |
| JP | 2014-225230 | A | 12/2014 |
| JP | 2014-228725 | A | 12/2014 |
| JP | 2014-228817 | A | 12/2014 |
| JP | 2015-1468 | A | 1/2015 |
| JP | 2015-504616 | A | 2/2015 |
| JP | 2015-49498 | A | 3/2015 |
| JP | 2015-506807 | A | 3/2015 |
| JP | 2015-508182 | A | 3/2015 |
| JP | 2015-72415 | A | 4/2015 |
| JP | 2015-075832 | A | 4/2015 |
| JP | 5696262 | B1 | 4/2015 |
| JP | 2015-088175 | A | 5/2015 |
| WO | 2006/098097 | A1 | 9/2006 |
| WO | 2011/045851 | A1 | 4/2011 |
| WO | 2013/049248 | A2 | 4/2013 |
| WO | 2013/111267 | A1 | 8/2013 |
| WO | 2015/030100 | A1 | 3/2015 |

OTHER PUBLICATIONS

U.S. Appl. No. 14/979,169, filed Dec. 22, 2015 Final Office Action dated Nov. 1, 2017.
U.S. Appl. No. 14/979,169, filed Dec. 22, 2015 Final Office Action dated Nov. 27, 2018.
U.S. Appl. No. 14/979,169, filed Dec. 22, 2015 Non-Final Office Action dated Jul. 11, 2019.
U.S. Appl. No. 14/979,169, filed Dec. 22, 2015 Non-Final Office Action dated Jul. 12, 2018.
U.S. Appl. No. 14/979,169, filed Dec. 22, 2015 Non-Final Office Action dated Jun. 2, 2017.
U.S. Appl. No. 15/685,766, filed Aug. 24, 2017 Final Office Action dated Dec. 11, 2018.
U.S. Appl. No. 15/685,766, filed Aug. 24, 2017 Non-Final Office Action dated Jul. 10, 2019.
U.S. Appl. No. 15/685,766, filed Aug. 24, 2017 Non-Final Office Action dated May 18, 2018.
U.S. Appl. No. 15/685,774, filed Aug. 24, 2017 Final Office Action dated Jul. 27, 2018.
U.S. Appl. No. 15/685,774, filed Aug. 24, 2017 Final Office Action dated Jul. 5, 2019.
U.S. Appl. No. 15/685,774, filed Aug. 24, 2017 Non-Final Office Action dated Dec. 31, 2018.
U.S. Appl. No. 15/685,774, filed Aug. 24, 2017 Non-Final Office Action dated Jan. 4, 2018.
U.S. Appl. No. 15/685,782, filed Aug. 24, 2017 Final Office Action dated Jul. 5, 2019.
U.S. Appl. No. 15/685,782, filed Aug. 24, 2017 Final Office Action dated Jun. 12, 2018.
U.S. Appl. No. 15/685,782, filed Aug. 24, 2017 Non-Final Office Action dated Dec. 31, 2018.
U.S. Appl. No. 15/685,782, filed Aug. 24, 2017 Non-Final Office Action dated Jan. 4, 2018.
U.S. Appl. No. 15/917,328, filed Mar. 9, 2018 Final Office Action dated Dec. 6, 2018.
U.S. Appl. No. 15/917,328, filed Mar. 9, 2018 Non-Final Office Action dated Jul. 5, 2019.
U.S. Appl. No. 15/917,328, filed Mar. 9, 2018 Non-Final Office Action dated May 18, 2018.
U.S. Appl. No. 15/917,328, filed Mar. 9, 2018 Notice of Allowance dated Jan. 31, 2020.
U.S. Appl. No. 15/917,332, filed Mar. 9, 2018 Final Office Action dated Dec. 11, 2018.
U.S. Appl. No. 15/917,332, filed Mar. 9, 2018 Non-Final Office Action dated May 18, 2018.
U.S. Appl. No. 16/851,088, filed Apr. 16, 2020 Non-Final Office Action dated Jun. 24, 2020.
U.S. Appl. No. 16/851,088, filed Apr. 16, 2020 Notice of Allowance dated Jan. 7, 2021.
U.S. Appl. No. 17/897,968, filed Aug. 29, 2022 Non-Final Office Action dated Jan. 20, 2023.
U.S. Appl. No. 17/897,968, filed Aug. 29, 2022 Notice of Allowance dated May 19, 2023.
JP 2023-061131 Office Action dated May 21, 2024.

\* cited by examiner

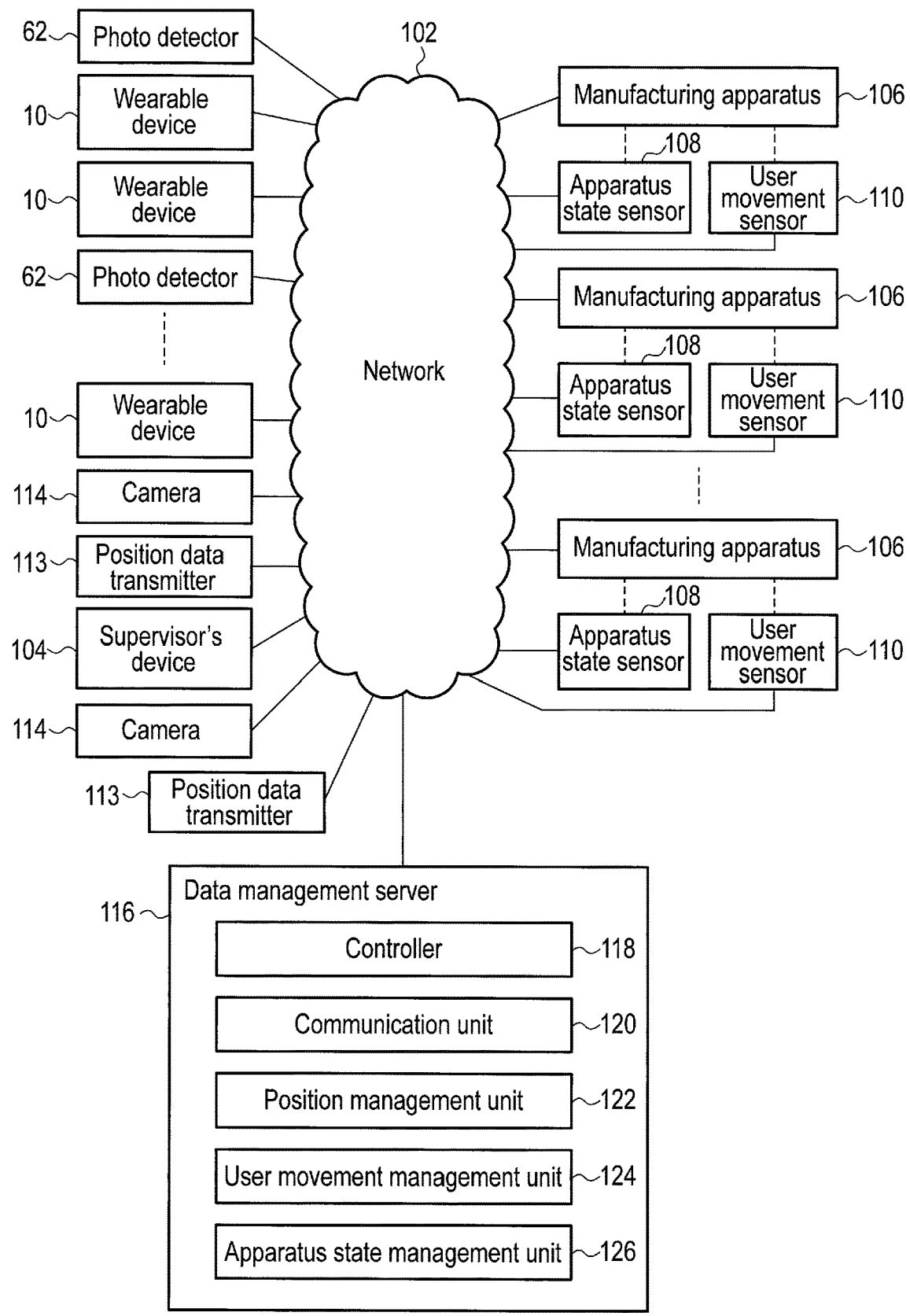
F I G. 6

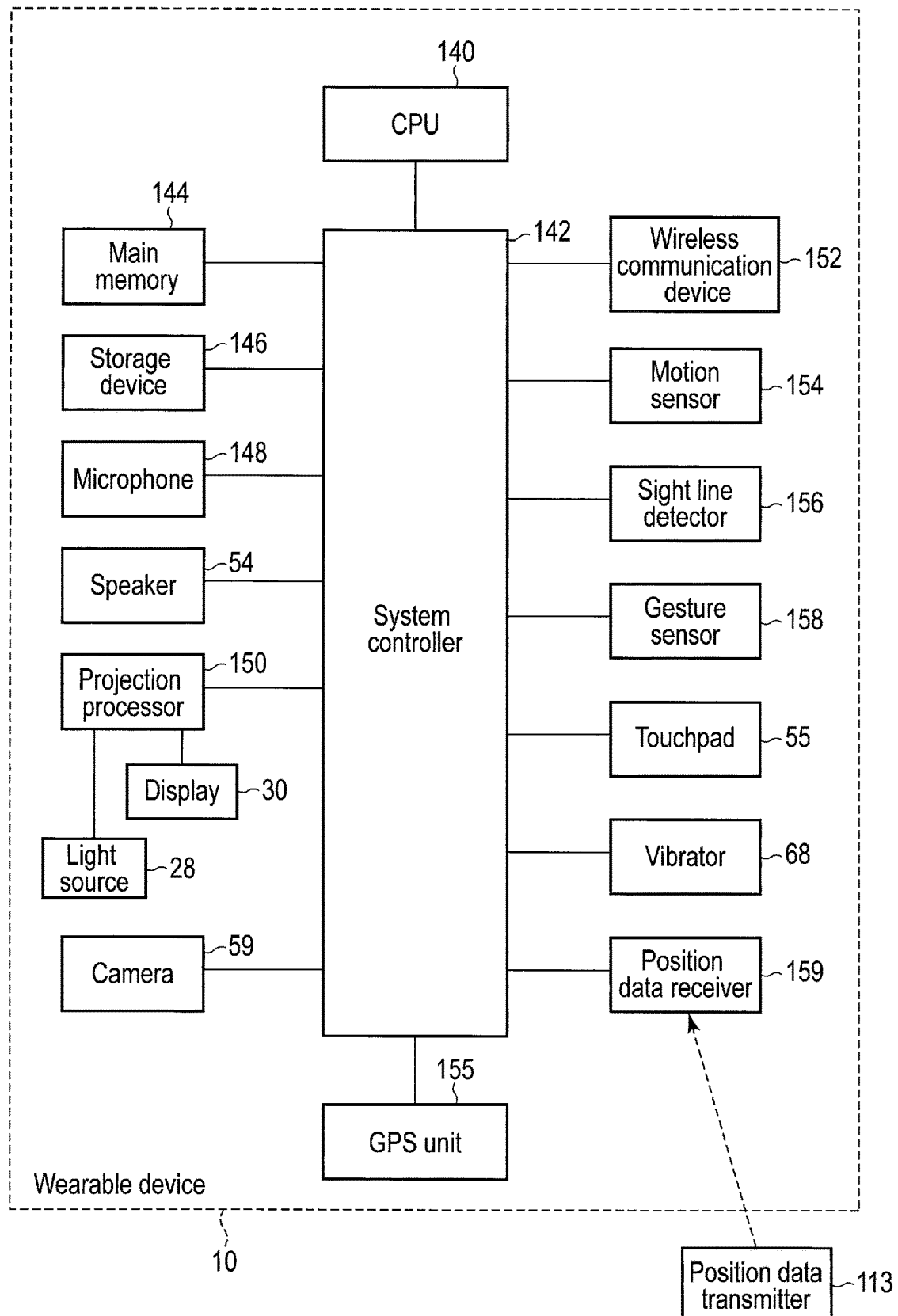
F I G. 7

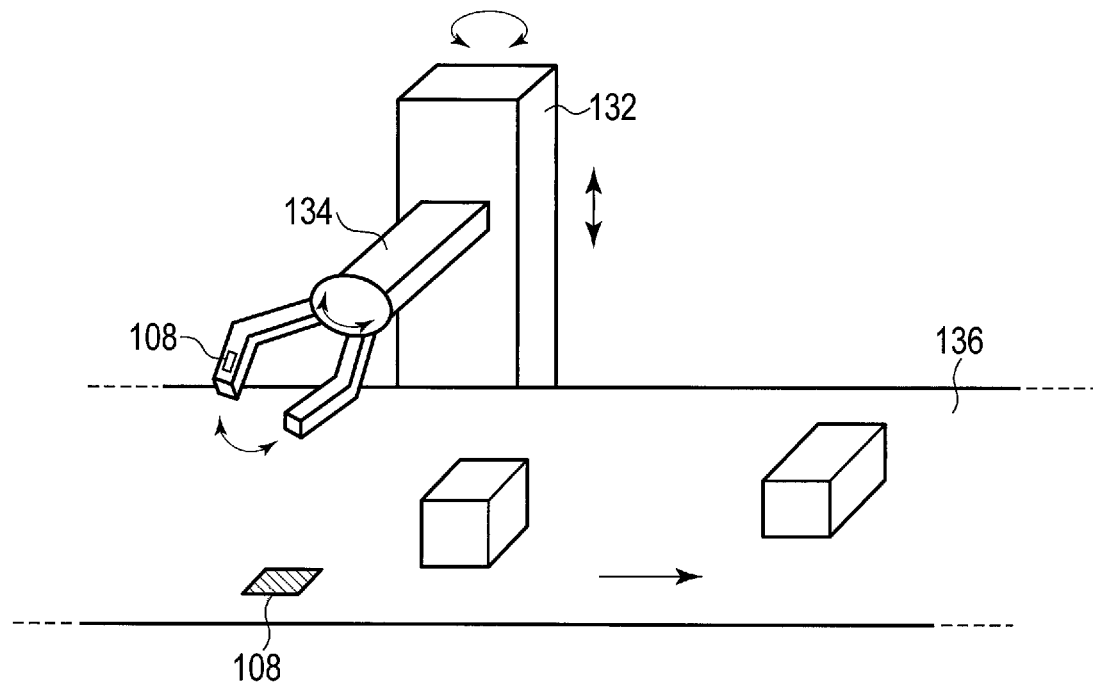
F I G. 8A
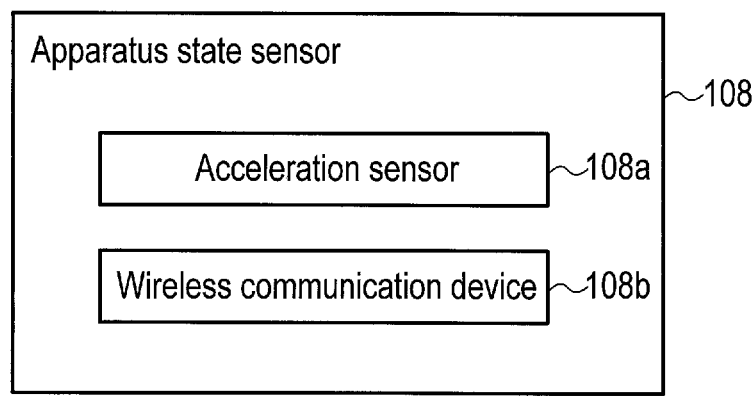
F I G. 8B

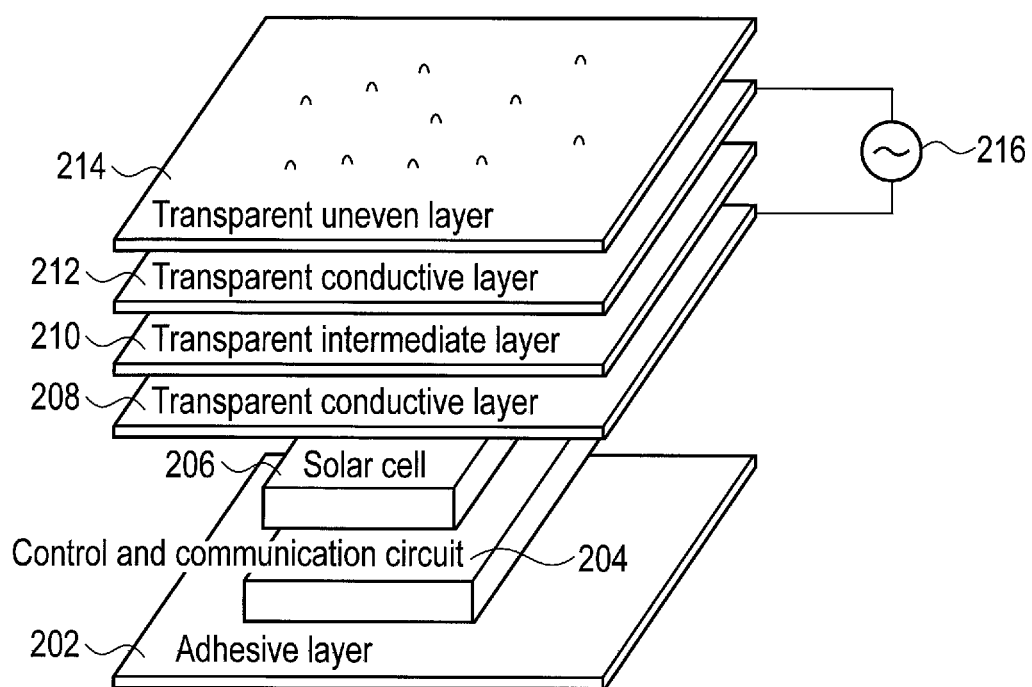
F I G. 11

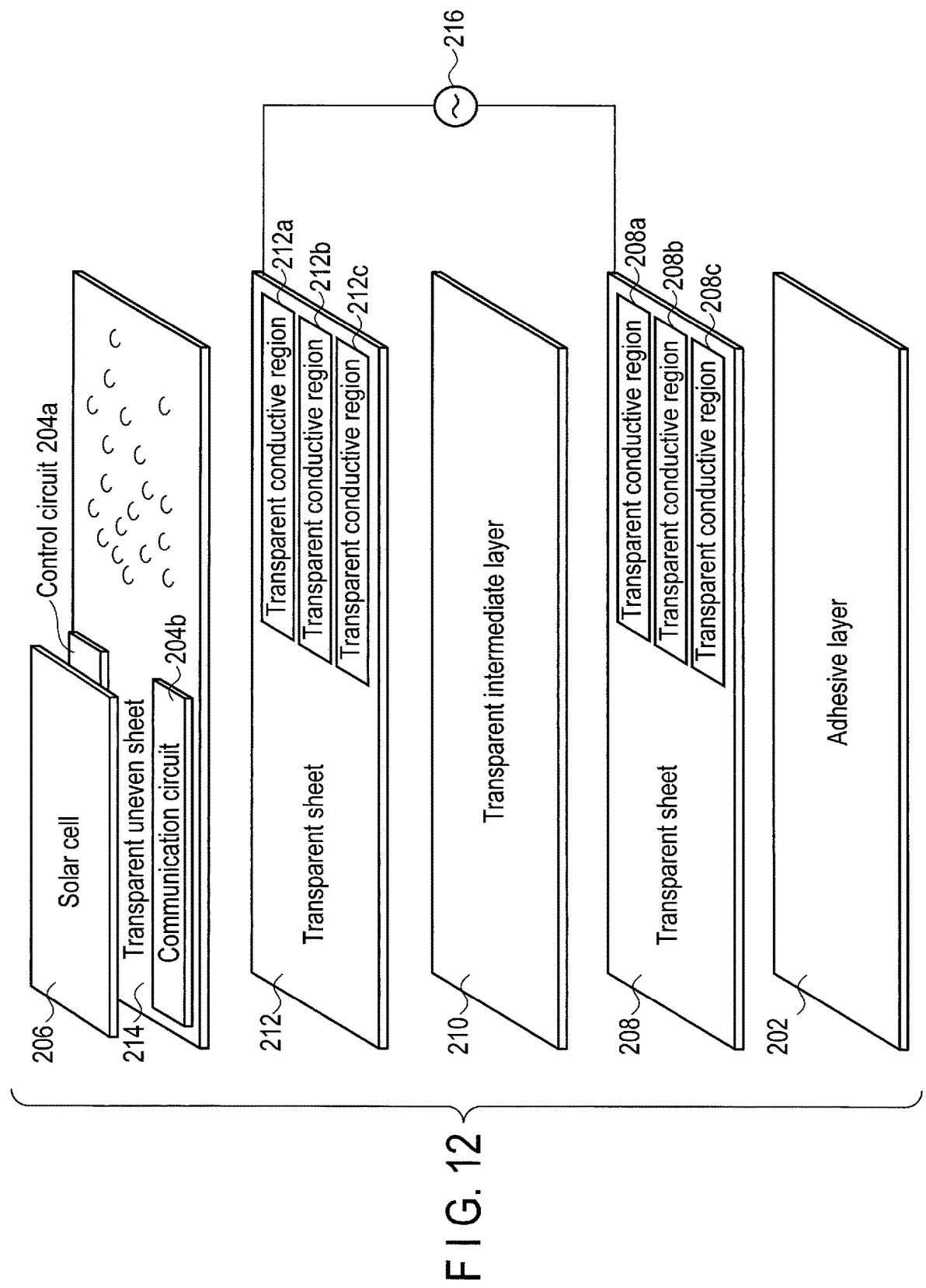
F I G. 12

| | Work Record |
|---|---|
| 15:28 | The thing put in the cart |
| 16:00 | The valve closed |
| 16:16 | The on/off switch flicked off |
| 16:18 | The first light switch flicked off |
| 16:20 | The third light switch flicked off |

SYSTEM AND METHOD DIRECTED TO AN EYEGLASSES-TYPE WEARABLE DEVICE

CROSS-REFERENCE TO RELATED APPLICATIONS

This application is a continuation of U.S. patent application Ser. No. 17/897,968, which is a continuation of U.S. application Ser. No. 17/210,420 filed Mar. 23, 2021, which is a continuation of U.S. application Ser. No. 16/851,088 filed Apr. 16, 2021, which is a divisional of U.S. patent application Ser. No. 15/685,766, filed Aug. 24, 2017, which is a divisional of U.S. patent application Ser. No. 14/979,169, filed Dec. 22, 2015, which claims the benefit of priority from Japanese Patent Application No. 2015-171933, filed Sep. 1, 2015, the entire contents of all of which are incorporated herein by reference.

FIELD

Embodiments described herein relate generally to a system and a method using an eyeglasses-type wearable device.

BACKGROUND

In manufacturing sites or manufacturing plants in which a large number of manufacturing apparatuses are operated, the operation rates of the manufacturing apparatuses have a great impact on production volumes. In a case where a usually-avoidable problem resulting from neglect of regular maintenance and checkups or an unexpected problem has occurred in a manufacturing apparatus but the problem has not been handled efficiently, the manufacturing apparatus cannot be operated for a long time, which leads to decreases in the operation rate and the production volume. Therefore, it is desired that the operation suspension time of a manufacturing apparatus is reduced as much as possible. In performing maintenance, checkups and repairs, since the maintenance, checkups and repairs vary from manufacturing apparatus to manufacturing apparatus, there are some cases where an operator refers to an instruction manual or a checklist (hereinafter referred to as a checklist) showing a workflow of each work step.

Recently, wearable devices have been actively introduced into manufacturing sites. In such a manufacturing site, for example, operators wear eyeglasses-type wearable devices and refer to checklists displayed on the lens surfaces. In this way, the operators no longer need to refer to paper checklists while working on apparatuses, and consequently the operators can have their work done efficiently even in the case of unfamiliar and complicated work without interruption of the work.

However, the operators still need to check against checklists to ensure completion of their work at each work step. Therefore, paper checklist are still prepared even although the operators electronically refer to checklists on the screens while working on the apparatuses, and the operators stop their work to fill in the paper checklists at the end of each work step. Since the operations of manufacturing apparatuses are kept stopped during that time, the production volumes decrease. Further, after returning their office, the operators write reports on their work based on the checklists. It is quite cumbersome for the operators to write such reports on their work.

There is a system for supporting an operator by using a head-mounted display with a built-in camera. As an example of the system, there is a medical-equipment management system which supports an operator of a medical device such as a used and contaminated endoscope or a piece of medical equipment such as a scalpel or forceps.

The system includes a head-mounted camera for capturing an image of the sight of an operator of a medical device or a piece of medical equipment; storage means for storing an image of the sight of an operator captured when the operator demonstrates the medical device or the medical equipment as a reference image; first determination means for comparing the image captured by the camera and the reference image read from the storage means in order to determine whether a predetermined operation is performed normally based on similarity between these two images; data output means for outputting data indicating an alarm or an instruction based on a determination result of the determination means; and output means for outputting the alarm or the instruction to the operator based on the data indicating the alarm or the instruction.

The system automatically recognizes the operation of the medical equipment operator by comparing the operation of the operator captured by the camera with the reference image prepared in advance. However, in this method, since the recognition accuracy of simple pattern match between images is low, complicated image processing such as feature extraction from the images is further required. Consequently, as the automatic recognition processing becomes highly complicated, a considerable amount of time will be required for the image processing.

The present embodiment aims to provide a system and a method for recognizing movements of a user of a wearable device quickly, simply and accurately and displaying content to support the user based on a recognition result.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 6 shows an example of a system including the wearable device and a data management server.

FIG. 7 exemplarily shows an electrical configuration of the wearable device.

FIG. 8A shows an example of detection of the state of an apparatus.

FIG. 8B shows an example of a sensor for detecting the state of an apparatus.

FIG. 11 is an exploded view showing an example of the structure of the sensor used in the system and for detecting movements of a user.

FIG. 12 is an exploded view showing another example of the structure of the sensor used in the system and for detecting movements of a user.

DETAILED DESCRIPTION

Various embodiments will be described hereinafter with reference to the accompanying drawings.

In general, according to one embodiment, a system includes a wearable device on a head of a user and including a display in a line of vision of the user, a first detector configured to detect a movement of the user, a second detector configured to detect a state of an apparatus operated by the user, and a server connected to the wearable device, the first detector and the second detector. The server is configured to display information about work contents of the user on the display based on a detection result of the first detector and a detection result of the second detector.

Wearable devices include head-mounted type wearable devices (such as eyeglasses, goggles and helmet types which may also be called an eyeglasses type collectively), wristband-type wearable devices, pendant-type wearable devices and the like. The following description is based on the assumption that the wearable device of the present embodiment is an eyeglasses-type wearable device. Eyeglasses-type wearable devices include optical head-mounted displays, which allow the user to see through their transparent lenses, and non-optical head-mounted displays, which block the view of the user and do not allow the user to see through them. In the following, optical head-mounted displays, which allow the user to see through them, will be taken as an example.

Figure 1:
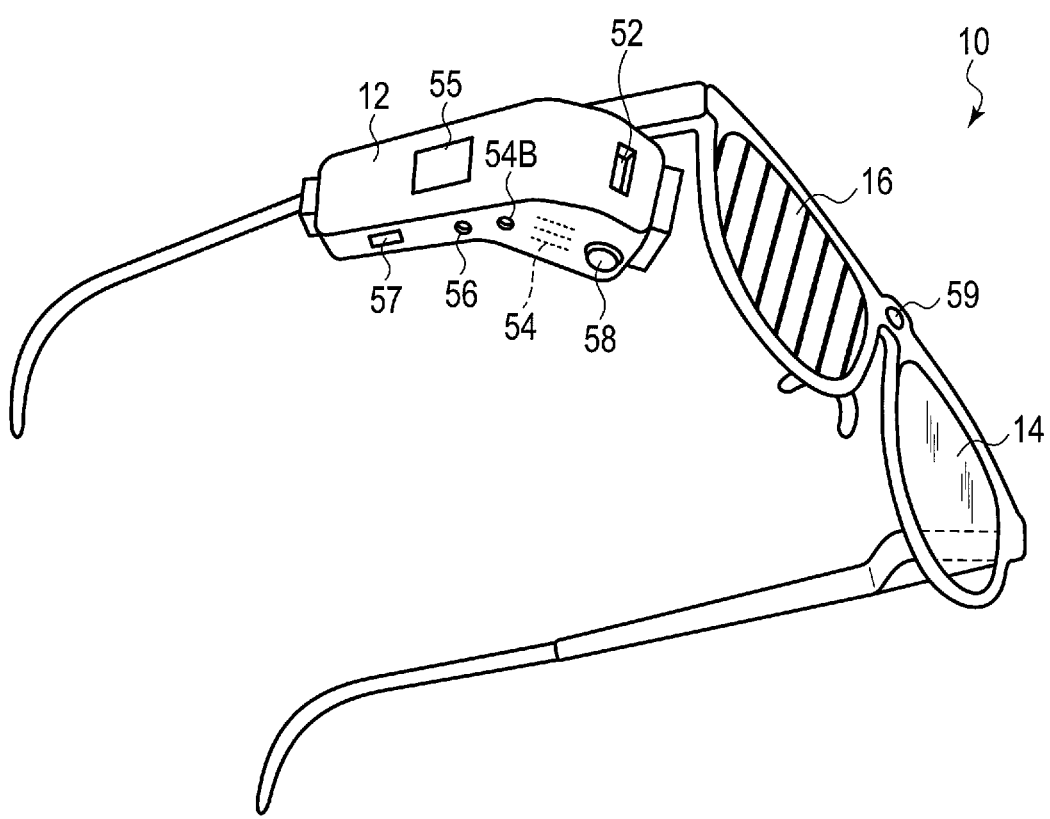
FIG. 1 is a perspective diagram showing an example of a wearable device of an embodiment.
Figure 2:
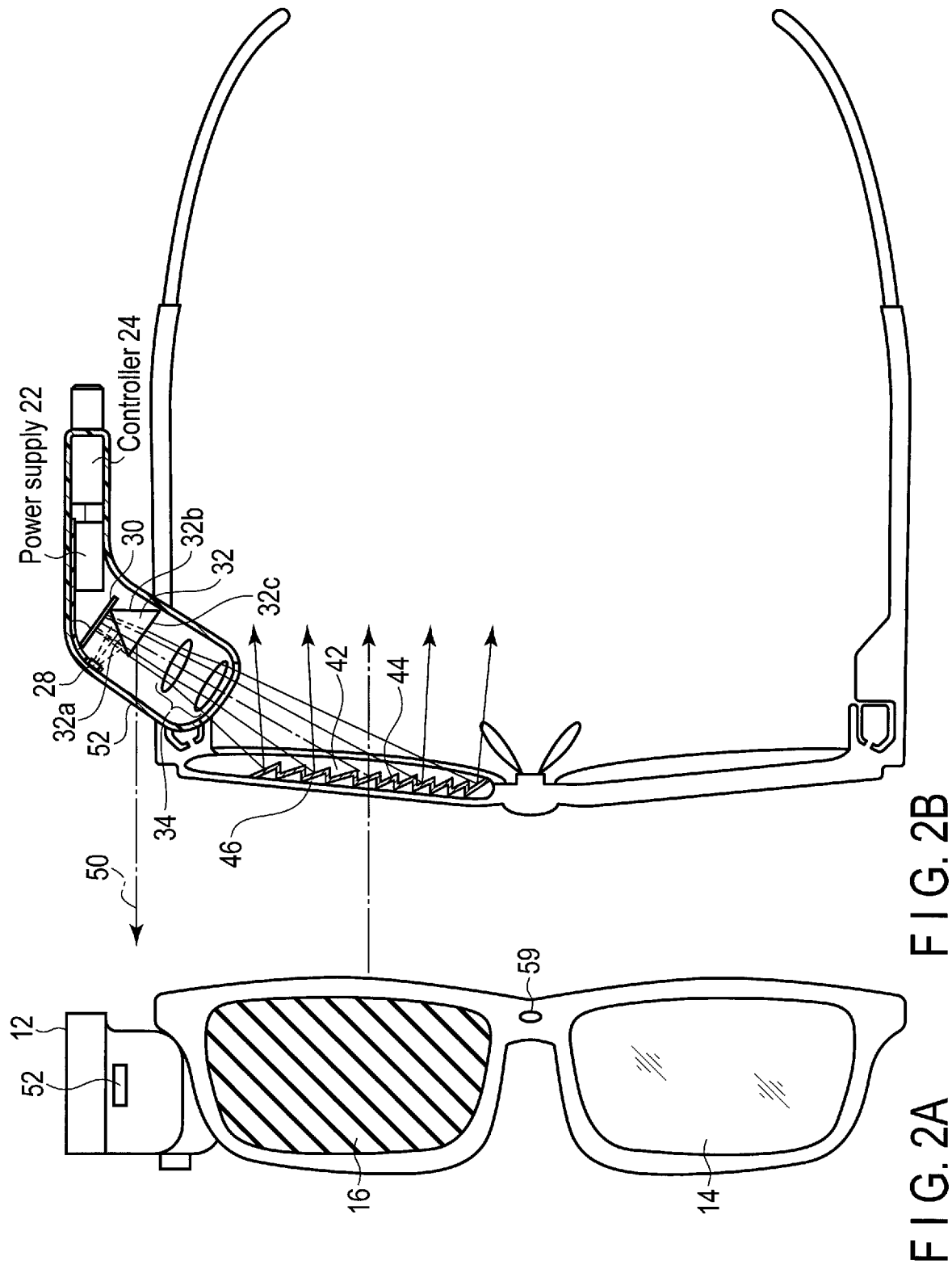
FIG. 2A shows a front view of an example of the wearable device.
FIG. 2B shows a cross-section structure of an example of the wearable device.

FIG. 1 is a perspective view of an eyeglasses-type wearable device (hereinafter referred to simply as a wearable device) 10, and FIG. 2A is a front view and FIG. 2B is a diagram showing a cross-section structure viewed from above.

The wearable device 10 has a shape substantially the same as that of an ordinary pair of glasses, but here a projector 12 is attached to the outside of the right-eye temple. Glasses 14 and 16 are set in the frame. The left-eye glass 14 is a normal transparent glass so that the user can see through the glass. The right-eye glass 16 is at least partly a screen 16. The screen 16 is configured to show an image projected by the projector 12 to the user. When the projector 12 is not projecting an image, the screen 16 is transparent and allows the user to see through the right-eye glass (screen) 16.

The projector 12 includes a power supply 22 and a controller 24 as electronic components. The power supply 22 includes a button battery, a rechargeable battery, a non-contact power supply secondary battery and the like. Alternatively, the projector 12 may not include a built-in battery but may be supplied with power from an external power supply via a power-supply line or a wireless channel. The controller 24 is configured to perform a communication with a server or another electronic device via a network which will be described later and thereby transmit and receive data. This communication may be a wired communication or may be a wireless communication. In the case of performing a wireless communication, Bluetooth (registered trademark), ZigBee (registered trademark), a short-range wireless communication such as UWB, a medium-range wireless communication such as WiFi (registered trademark) or a long-range wireless communication such as 3G/4G or WiMAX (registered trademark) may be used according to the usage environment.

The projector 12 further includes a light source 28, a display 30, a prism 32, a set of lenses 34 and the like as optical components. The light source 28 may be a dimming white LED light source having several, for example, three light emitting diodes having luminescent colors different from each other and amounts of output light respectively variable. According to the dimming white LED light source, even if the wearable device 10 is used in such an environment as a clean room using light having a luminescent color consisting principally of orange, a clear projection image can be obtained by changing the luminescent color of the LED light source based on the usage environment. Further, according to the dimming white LED light source, it is possible to output a display color easy for the user to see, and thus as compared to the case of outputting a display color difficult for the user to see, the causes of troubles to the user such as eye strain and migraine associated with eye strain can be prevented.

The display 30 is, for example, a reflective liquid crystal display (LCD) module and configured to display a predetermined text, image and the like (hereinafter referred to also as a display image collectively) based on display control executed by the controller 24. Non-parallel light (hereinafter referred to also as diverging light) output from the light source 28 is reflected on a half mirror surface 32a of the prism 32, and thereby illuminates a display image of the display 30. The reflected light of the display 30 is, after passing through the half mirror surface 32a as light indicative of the display image (hereinafter referred to also as image light), output from the outgoing surface 32c and then projected on the screen 16 as a projection image in a predetermined size via the set of lenses 34.

The screen 16 includes a near-side transparent refractor 42, a Fresnel-lens-type half mirror surface 44 and a back-side transparent refractor 46. The image light reaching the half mirror surface 44 is partly reflected on the half mirror surface 44 and forms a visual image (projection image) indicative of the display image of the display 30 at a few meters away. Note that, since the screen 16 allows the user to partly see through the screen 16, it is also possible to configure the screen 16 to show the projection image as well as the view in front of the user.

A part of the image light (diverging light) output from the light source 28 and passing thorough the half mirror surface 32a is totally reflected on the total-reflection surface 32b and becomes leaking light 50 of the diverging light from the light source 28 refracted in the outgoing surface 32c. The leaking light 50 is output in a direction different from the direction of the screen 16 through an opening or a gap (leading portion) 52 formed on the front side of the projector 12.

The wearable device 10 includes a speaker 54A, an earphone jack 54B, a microphone jack 56, a sliding switch 57, a rotating switch 58 and the like in a predetermined portion, for example, in a bottom portion of the projector 12. The microphone jack 56 is connected to a hands free microphone (not shown in the drawing) and collects the user's voice. The sliding switch 57 is configured, for example, to adjust the brightness, color tone and the like of the projection image of the projector 12. The rotating switch 58 is configured, for example, to adjust the projection angle and the like of the projection image. With such a configuration as to set different adjustment values by different operations such as by operating the sliding switch 57 and the rotating switch 58, the user can adjust the projection image by performing touch operations while looking at the projection image. For example, by operating the sliding switch 57, it is possible to provide the projection image having the display brightness and color tone of the user's taste. By operating the rotation switch 58, it is possible to adjust the projection angle so that the projection image is displayed in the most appropriate position based on the shape or size of the user's head. Note that the objects to be adjusted by the sliding switch 57 and the rotating switch 58 may be opposite to each other, the positions of the sliding switch 57 and the rotating switch 58 may be opposite to each other, or their functions may be assigned to a single operation member configured to perform two kinds of operations.

Although it is possible to perform adjustment using these switches 57 and 58 in a trial-and-error process while looking at the projection image, to improve the efficiency of adjustment, it is also possible to perform adjustment by projecting a menu image and selecting an item on the screen. When the display 30 displays a menu image, the menu image is projected on the screen 16.

Further, a menu item may not be selected by an operation on the switch 57 or 58 but may be selected by a touch operation. Therefore, a touchpad 55 is further provided on the outside of the projector 12. When a menu or the like is displayed by the display 30, the user can input an operation easily and efficiently by touching a position of the touchpad 55 corresponding to the display position of an item in the menu.

A camera 59 is provided in the center front on the outside and configured to capture an image of the front view (still image and moving image). Note that, although not shown in the drawing, it is possible to provide another camera in the center front on the inner side to face the user and configure to capture the eyeballs of the user to detect the irises of the user. The irises can be used for user authentication.

By using the leaking light 50 from the wearable device 10, the state of the wearable device 10, that is, the state of the user can be detected. With reference to FIGS. 3, 4 and 5A-5K, the principle of detecting the state of the wearable device will be described. Here, the state includes a position, a shift of the position and the like.

Figure 3:
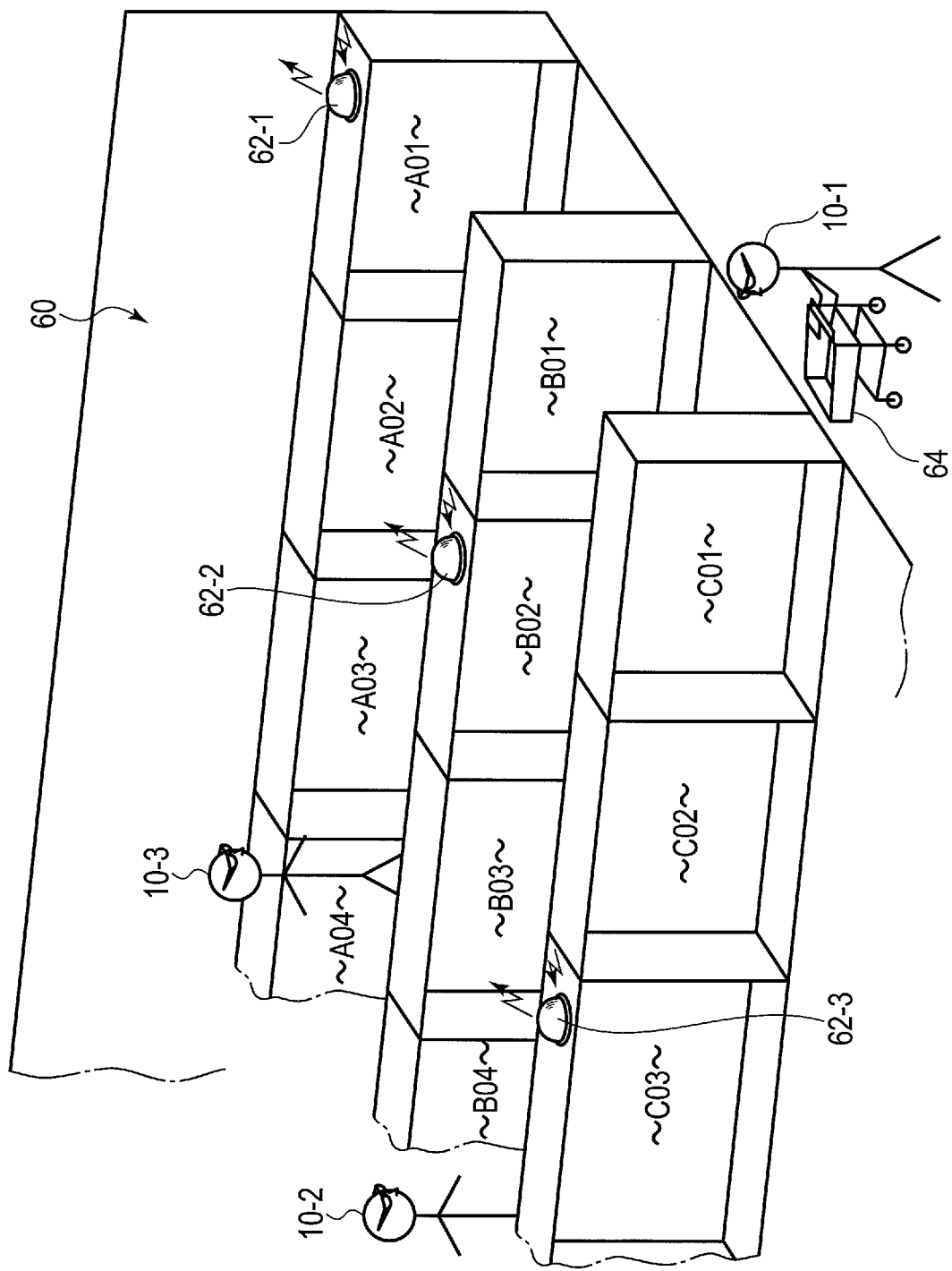
FIG. 3 shows an example of position detection of the wearable device.

An example of the use of the wearable device is shown in FIG. 3. For example, in a work area 60 of, for example, a component yard of a plant, a product warehouse of a mail-order firm or a delivery department of a retailer, a given number of work spaces or product shelves A01 to Axy (x and y are both positive integers), B01 to Bxy and C01 to Cxy are arranged. The work spaces or the product shelves may be, for example, work tables in a plant, manufacturing apparatuses in a production line, desks at school, seating positions in a conference room, and the like.

In the work area 60, at least one photo detector 62-1 to 62-n (n is a positive integer) is installed. The at least one photo detector 62-1 to 62-n is configured to detect the positions (x, y, z), the numbers, the shifts of the positions, the changes of the directions and the like of the wearable devices 10-1 to 10-m (m is a positive integer) respectively by a detection method shown in FIGS. 4 and 5A-5K. By detecting the positions, the numbers, the shifts of the positions, the changes of the directions and the like of the wearable devices 10-1 to 10-m, the states such as the positions and the shifts of the positions of a given number of the users of the wearable devices 10-1 to 10-m can be recognized.

The users can move around the work area 60 freely. The users perform predetermined work in predetermined positions, namely, work spaces 64 such as stations (carts), or containers or movable tables equivalent thereto. Note that the work space 64 is not necessarily movable but may be a fixed desk, a seating position or the like.

Figure 4:
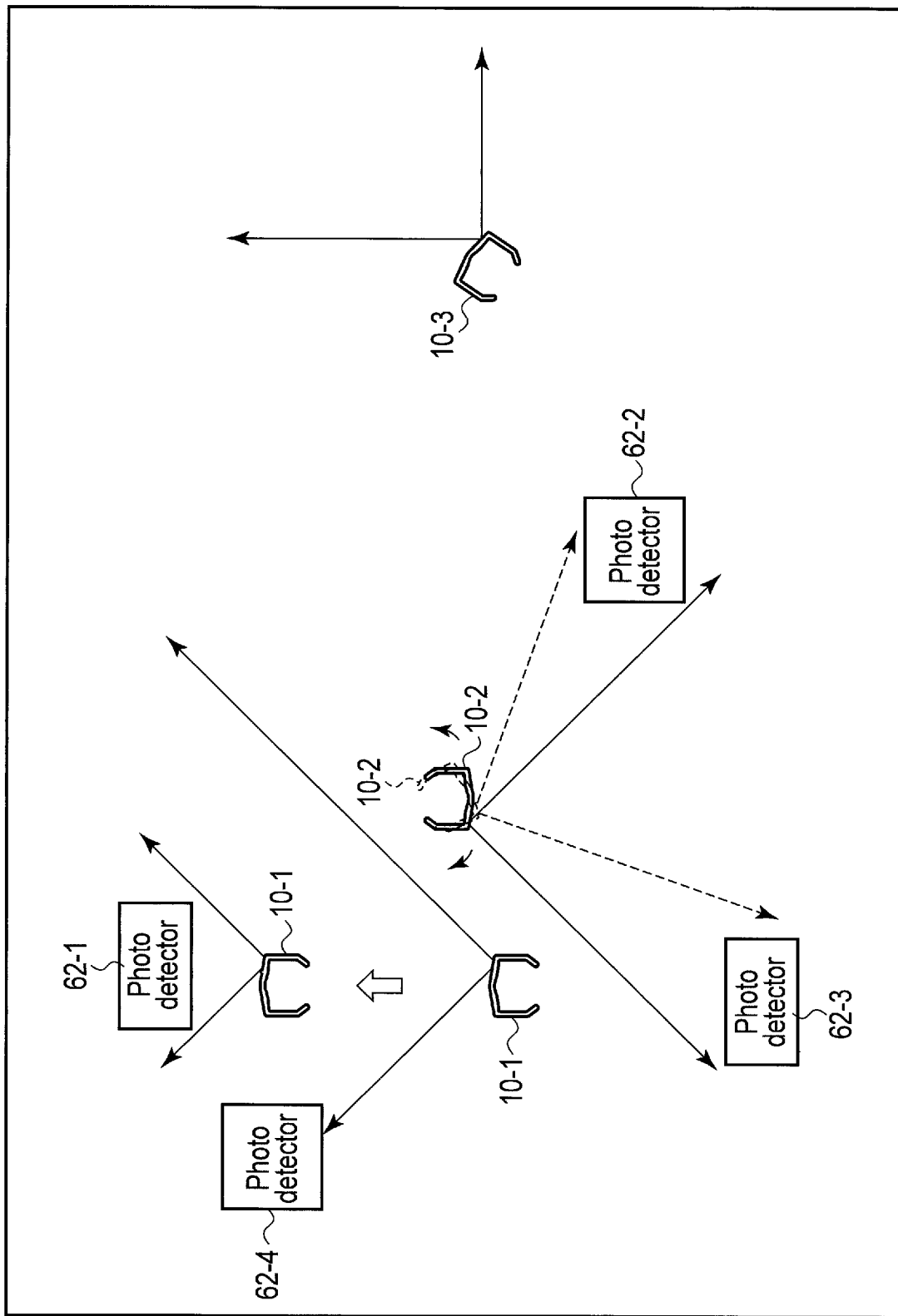
FIG. 4 exemplarily shows the principle of the position detection of the wearable device.

As shown in FIGS. 3 and 4, a detection system includes at least one wearable device 10 and at least one photo detector 62. The photo detector 62 has a function of detecting the leaking light 50 and a function of performing communication to transmit a detection result to a server or the like. The communication function may be a wired communication function or may be a wireless communication function as in the case of the communication function of the wearable device 10. In the case of a wireless communication, Bluetooth (registered trademark), ZigBee (registered trademark), a short-range wireless communication such as UWB, a medium-range wireless communication such as WiFi (registered trademark) or a long-range wireless communication such as 3G/4G or WiMAX (registered trademark) may be used according to the usage environment. In the present embodiment, various units and modules having communication functions will be described below, and these communication functions may be wired communication functions or may be wireless communication functions similarly. In the case of a wireless communication, Bluetooth (registered trademark), ZigBee (registered trademark), a short-range wireless communication such as UWB, a medium-range wireless communication such as WiFi (registered trademark) or a long-range wireless communication such as 3G/4G or WiMAX (registered trademark) may be used according to the usage environment.

The wearable device 10 intermittently modulates the leaking light 50 by using data including identification data of the device (hereinafter referred to also as a device ID) so that the photo detector 62 can identify the wearable device 10 based on the received leaking light 50. Although a typical example of the modulation method is a chopper modulation method of decreasing an amount of luminescence to zero, the following description is based on the assumption that the wearable device 10 adopts a modulation method of ensuring a predetermined or more amount of luminescence even in the case of light having a small amount of luminescence. In this way, the strain on the user's eyes can be reduced. In the case of adopting a digital sum value (DSV) free modulation method (that is, a method of calculating the DSV of a modulation signal constantly, inserting an appropriate bit inversion code and setting a direct-current component to zero) as a modulation method, it is possible to prevent a change in the amount of luminescence over a relatively long range and thereby keep a change in the amount of luminescence macroscopically zero, and thus the strain on the user's eyes can be further reduced. Since the human eyes can perceive a change up to about second, it is possible to achieve the effect of reducing the strain of the user's eyes by setting the reference frequency of the above-described modulation to, for example, greater than or equal to 20 Hz, more preferable, greater than or equal to 60 Hz. On the other hand, since the LED used for the light source 28 has an internal impedance and a connecting capacity, the frequency of less than 100 MHz, more preferably, less than or equal to MHz is desirable for performing highly-accurate modulation. From the above, it is desirable that the modulation frequency of the light source 28 used in the detection system of the present embodiment be 10 Hz to 100 MHz, more preferable, 10 Hz to 10 MHz.

Since the leaking light 50 of the diverging light from the light source 28 is used, the amount of light detected by the photo detector 62 varies depending on the distance between the wearable device 10 and the photo detector 62. By using this phenomenon, the distance between the wearable device 10 and the photo detector 62 or the direction of the wearable device 10 with respect to the photo detector 62 can be obtained. Since the position (including the level) of the photo detector 62 is fixed, as the distance between the photo detector 62 and the wearable device 10 is obtained, the position of the wearable device 10 ($x, y, z$) can be detected accordingly.

Further, by using the leaking light 50 of the diverging light from the light source 28, detection of the leaking light 50 can be performed in a relatively wide area. As a result, by installing only a relatively small number of the photo detectors 62-1 to 62-$n$, the positions of the wearable devices 10-1 to in the work area 60, the distances between the wearable devices 10 and the photo detectors 62, the directions of the wearable devices 10, or the directions of the wearable devices 10 with respect to the photo detectors 62 can be detected. Consequently, the installation cost required for installing the detection system can be reduced.

The data of amounts of the leaking light 50 detected by the photo detectors 62 is transmitted from the photo detectors 62 to a server which will be described later at a predetermined time. The server analyzes the data collected from the photo detectors 62. In this way, the positions and the states of the desired wearable devices 10-1 to 10-$m$, more specifically, the states of the users can be detected.

FIG. 4 is a schematic diagram showing a specific example of the use of the system for recognizing the wearable device of the embodiment. The following description is based on the assumption that there are three users wearing wearable devices 10-1 to 10-3 around four photo detectors 62-1 to 62-4. The leaking light 50 from the wearable devices 10-1 and 10-2 is detected by the photo detectors 62-1 to 60-4. The photo detectors 62-1 to 62-4 perform analog-to-digital conversion of the amounts of the leaking light 50 detected respectively and transmit them to a server as light amount data indicative of the amounts of light at a predetermined time, for example, by a short-range wireless communication.

The following description is based on the assumption that the position of the wearable device 10-1 is shifted toward the photo detector 62-1 as the user moves toward the photo detector 62-1 and meanwhile the direction of the wearable device 10-2 is temporarily changed as the user makes a given movement such as turning of the head (rotating of the head). The changes in the detection data occurring at this time is shown in FIGS. 5A-5K.

FIGS. 5A-5K illustrate the case of using an intermittent time-shift method as a modulation method of the leaking light 50 of the wearable devices 10-1 to 10-3. That is, ID modulation times are set respectively to the wearable devices 10-1 to 10-3 in a staggered manner.

Figure 5:
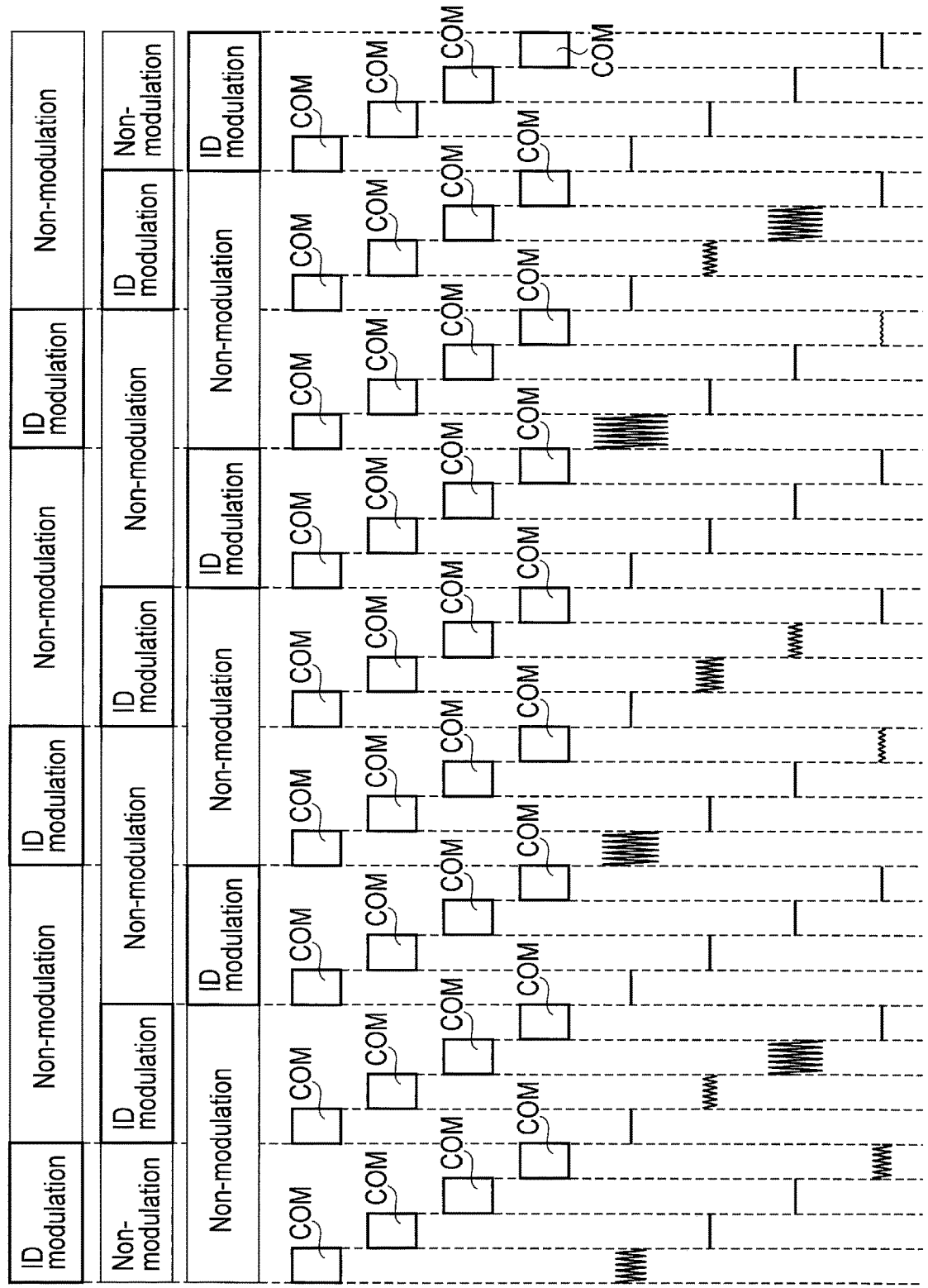
FIGS. 5A, 5B, and 5C show an example of operation periods of the wearable devices.
FIGS. 5D, 5E, 5F, and 5G show an example of communication periods of the photo detectors.
FIGS. 5H, 5I, 5J, and 5K show an example of signal waveforms of the photo detectors.

As shown in FIGS. 5A, 5B, and 5C, intermittent ID modulation times are set respectively to the first to third wearable devices 10-1 to 10-3, and the other times are set as non-modulation times. In each ID modulation time, a synchronization signal SYNC is paired with each of the device IDs of the wearable devices 10-1 to 10-3 (on a one-to-one basis), and the pairs are repeated for several times (multiples of four times in the case where there are four sensors as shown in FIGS. 5D-5G).

As the non-modulation time of the first wearable device 10-1 starts, the ID modulation time of the second wearable device 10-2 starts. Similarly, as the non-modulation time of the second wearable device 10-2 starts, the ID modulation time of the third wearable device 10-3 starts.

In the ID modulation time of the second wearable device 10-2 and the ID modulation time of the third wearable device 10-3, the synchronization signal SYNC and the device ID of the wearable device 10-2 or 10-3 are repeatedly modulated. By superimposing the device ID of the wearable device 10 on a modulation signal in this way, the device ID can be detected.

In the above-described case, the modulation times of the respective wearable devices 10-1 to 10-3 are set on a time-division basis (on an intermittent basis). However, for example, it is also possible to perform modulation successively for all the wearable devices 10-1 to 10-3 and change the modulation reference frequencies of the wearable devices 10-1 to 10-3 respectively. Further, it is also possible to change the characteristics of the frequency spectrums in spread spectrum, respectively.

As shown in FIGS. 5D-5G, each ID modulation time is divided into sections of the data communication times (COMs) with the photo detectors 62-1 to 62-4.

As shown in FIG. 4, a part of the leaking light from the wearable device reaches the photo detector 62-4 at the beginning. Therefore, as shown in FIG. 5K, the photo detector 62-4 detects the leaking light from the wearable device 10-1 at the beginning. However, as the position of the wearable device is shifted toward the photo detector 62-1, the modulation signal amplitude of the leaking light from the wearable device 10-1 detected by the photo detector 62-4 decreases. On the other hand, as shown in FIG. 5H, the modulation signal amplitude of the leaking light from the wearable device 10-1 detected by the photo detector 62-1 increases as time advances. By comparing the changes of the modulation signal amplitudes detected by the photo detectors 62-1 to 62-$n$ with time, the changes (shifts) of the positions of the detection targets, namely, the wearable devices 10-1 to 10-$m$ with time can be detected.

Meanwhile, the wearable device 10-2 is directed to the photo detector 62-3 at the beginning, and thus with regard to the modulation signal amplitude of the leaking light, the detection value of the photo detector 62-3 is greater than the detection value of the photo detector 62-2. Here, suppose that the second user then turns the head and the wearable device 10-2 is temporarily directed to the photo detector 62-2. In this case, the detection output of the wearable device 10-2 output from the photo detector 62-2 temporarily increases and then decreases as shown in FIG. 5I. On the other hand, the detection output of the wearable device 10-2 output from the photo detector 62-3 temporarily decreases and then increases as shown in FIG. 5J.

In this way, by comparing changes in the modulation signal amplitudes detected by the photo detectors 62 with time, changes in the directions of the detection targets, namely, the wearable devices 10-1 to 10-$m$ can be detected.

In the above-described detection, such movements of the user as moving from one place to another or turning the head are used. However, the above-described case is in no way restrictive, and various other movements of the user may also be used for detection. For example, as the user makes such movements as moving his or her hands or twisting the upper part of the body, the leaking light may be blocked temporarily. In that case, all the modulation signal amplitudes of the photo detectors 62-1 to 62-4 temporarily decrease in the same period of time. In this way, by comparing the relationships among changes in the modulation signal amplitudes of all the photo detectors 62-1 to 62-4, various movement patterns of the user can be identified.

According to the above-described method, not only the movements of the user but also the will of the user can be recognized.

Note that, as a method of detecting the position (x, y, z) of the wearable device 10, it is also possible to use a beacon. In the above-described case, the position or state of the wearable device 10 is detected by executing comparative processing of device identification data output from a number of wearable devices 10 as modulated light and received by a number of photo detectors 62. However, by installing a number of position data transmitters in the work area 60 and transmitting beacons according to the installation positions from the transmitters by, for example, a short-range wireless communication with a communication range of a few meters such as RF-ID, it is also possible to detect the wearable device 10 which receives a beacon to be in a position substantially the same as the position of the transmitter having transmitted that beacon. Further, it is also possible to detect the position of a wearable device by using the GPS. The position detection is not necessarily based on a single method but may be based on a plurality of methods to improve detection accuracy.

FIG. 6 is a diagram showing an example of the whole system using the wearable device. Here, a case where the system is applied to a manufacturing site of a manufacturing plant will be described. A plurality of wearable devices 10, a plurality of photo detectors 62 of FIG. 3, at least one supervisor's device 104, a plurality of manufacturing apparatuses 106, at least one camera 114, a data management server 116 are connected to a network 102. The network 102 may be provided, for example, on a plant building, a department, a floor or a business office basis, or may be a network installed in each plant, each building or each company or the Internet. In a case where there is a plurality of manufacturing sites in a single plant, the network of a manufacturing site of FIG. 6 may constitute a LAN, and a plurality of LANs may be connected to the network of the whole plant. The network 102 may be a wireless network or may be a wired network.

There are a number of operators in a manufacturing site, but not all the operators wear the wearable devices 10. Therefore, the wearable devices 10 may not be prepared for all the operators, but only a predetermined number of wearable devices 10 may be prepared and the operators wear available shared wearable devices when needed. The system needs to identify the user if the user puts on the wearable device. This is because the system displays, for the user working on a specific manufacturing apparatus, the workflow of the manufacturing apparatus or makes a report on the work based on the user's movements. There are various methods of identifying the user, but the user may input the user's ID and the device ID from a device not shown in the drawing when the user puts on the wearable device 10. The input operation is not necessarily a key input but may be an audio input from a microphone or a scan input using a bar code. Further, since it is likely that the user has his or her own unique way of putting the device on, it is possible to detect the user by detecting the user's movements made at this time. The feature quantities indicating the user's movements can be obtained from acceleration or angular velocity of the wearable device 10, movements of the face, hands or fingers of the user, or environmental sounds collected by a microphone. For example, it is possible to recognize the state of the wearable device based on friction sounds between the temple and the skin or the hairs produced when the user puts on or takes off the wearable device 10.

There is at least one supervisor for the operators in the manufacturing site, and the supervisor uses the supervisor's device 104. Since the supervisor does not need to move around, the supervisor's device 104 may have a structure the same as that of the wearable device 10 or may have a structure the same as that of an ordinary personal computer or an ordinary tablet computer, and description of the supervisor's device 104 will be omitted.

To each manufacturing apparatus 106, an apparatus state sensor 108 and a user movement sensor 110 are attached. These sensors 108 and 110 have communication functions and are connected to the network 102.

The camera 114 constantly captures moving images of the users in the manufacturing site. By analyzing the images, the movements of the users can be detected. For example, the user of the wearable device 10 can be identified by storing reference images for the respective users in advance and comparing an image of the user putting the wearable device 10 on or an image of the user taking the wearable device 10 off with the reference images. When it is difficult to install an enough number of cameras to cover the whole manufacturing site at a time, a few number of cameras 114 each having a variable angle of view and configured to capture an image of the users in a wider area may be installed instead.

The data management server 116 includes a controller 118, a communication unit 120, a position management unit 122, a user movement management unit 124, an apparatus state management unit 126 and the like. The communication functions of the sensors 108 and 110, the communication function of the supervisor's device 104, the communication function of the camera 114 and the communication function of the communication unit 120 may be wired communication functions or may be wireless communication functions as in the case of the communication function of the wearable device 10. In the case of a wireless communication, Bluetooth (registered trademark), ZigBee (registered trademark), a short-range wireless communication such as UWB, a medium-range wireless communication such as WiFi (registered trademark) or a long-range wireless communication such as 3G/4G or WiMAX (registered trademark) may be used according to the usage environment.

The position management unit 122 is configured to collect data of the positions of the wearable device 10 and the supervisor's device 104 based on the outputs of the photo detector 62 and various sensors of the wearable device 10 and the supervisor's device 104 at regular intervals. Further, the position management unit 122 is configured to identify the user of the wearable device 10 or the supervisor's device 104, and manage the device ID, the user ID and the position of the wearable device 10 or the management device 104.

The user movement management unit 124 is configured to collect data of the movements and state of the user of the wearable device 10 based on the outputs of the photo detectors 62, various sensors of the wearable devices 10, and the user movement sensor 110 of the manufacturing apparatus 106 and manage the device ID, the user ID, and the movements and state of the wearable device 10. The apparatus state management unit 126 is configured to collect data of the state of the manufacturing apparatus based on the output of the apparatus state sensor 108 of the manufacturing apparatus 106 at regular intervals and manage the data. Note that it is possible to configure the apparatus state sensor 108 to notify, if there is a change in the state of the apparatus, the change to the apparatus state management unit 126 and collect data of the state of the manufacturing apparatus.

The data management server 116 is configured to notify, if the apparatus state management unit 126 detects that a manufacturing apparatus has a problem, data of the position having the problem and state of the manufacturing apparatus to the management device 104. At the same time, the states of the operators are determined, and candidate operators who can deal with the apparatus having a problem most efficiently are extracted and presented to the supervisor's device 104.

The present embodiment relates generally to a technique of automatically making a work checklist and presenting it to the user and of automatically checking off a corresponding item in the checklist as the user completes each work step. Therefore, the data management server 116 integrates the data obtained from the plurality of sensors 108 and 110 connected to the network 102 or various sensors of the devices 10 and 104 and performs a computation to automatically detect and recognize the movements of each operator. The data management server 116 makes a workflow (checklist) based on the result and supports an automatic input (automatic entry) to a corresponding portion in the checklist. The data management server 116 automatically makes a work report when completing an automatic input (automatic entry) to the last item in the work checklist.

The contents of the above-described work checklist vary depending on the manufacturing apparatus subjected to maintenance. Further, the contents of the above-described work checklist also vary depending on the portion in a manufacturing apparatus having a problem. Therefore, the data management server 116 collects data related to the manufacturing apparatus requiring maintenance from the manufacturing state sensor 108, and automatically detects and recognizes the portion in the manufacturing apparatus having a problem. The data management server 116 then automatically identifies the wearable device 10 of an operator who is to perform maintenance and displays the contents of the maintenance on the device 10 in a work checklist form.

FIG. 7 is a diagram showing an example of the electrical configuration of the wearable device 10. The wearable device 10 includes a CPU 140, a system controller 142, a main memory 144, a storage device 146, a microphone 148, the speaker 54, a projection processor 150 (configured to control the light source 28 and the display 30), the camera 59, a wireless communication device 152, a motion sensor 154, a sight line (line of vision) detector 156, a gesture sensor 158, the touchpad 55, a vibrator 68, a position data receiver 159, a GPS unit 155 and the like.

The CPU 140 is a processor configured to control various modules in the wearable device 10 and execute computer programs loaded from the storage device 146 including a nonvolatile semiconductor memory such as an SSD or a flash array to the main memory 144. The programs include an operating system (OS) and various application programs. The CPU 140 executes, for example, the following processing by executing the application programs and performing communication with the data management server 116 via the network 102 using the wireless communication device 152. For example, the CPU 140 executes various kinds of control such as control to input a voice by the microphone 148 and transmit the audio data to the data management server 116, control to capture an image by the camera 59 and transmit the image data to the data management server 116, control to transmit input data from the motion sensor 154, the sight line detector 156, the gesture sensor 158, the touchpad 55 or the position data receiver 159 to the data management server 116, control to play a sound by the speaker 54 or stereo earphones (not shown) connected to the earphone jack 54B, and control to vibrate the vibrator 68. Although the description is based on the assumption that the speaker 54 is a monaural speaker, it is possible to further provide a speaker (not shown in the FIGS. 1 and 2) in the left-eye temple when a stereo speaker is required.

The system controller 142 is a device configured to connect the local bus of the CPU 140 and various components. The microphone 148 is connected to the microphone jack 56 and configured to collect user's voices or environmental sounds. By recognizing user's voices or analyzing environmental sounds, it is possible to detect movements of the user and thereby identify the user. For example, by storing reference voices of respective users in advance and comparing the voice of the wearer with the reference voices, the wearer can be identified. Further, the work area the wearer is in can be identified by analyzing environmental sounds. The speaker 54 is configured to output an alarm or the like to attract the user's attention. The projection processor 150 is configured to output an image signal to the display 30 and project an image of the display 30 on the screen 16 by lighting the light source 28. The image includes not only a still image but also a moving image. The wireless communication device 152 includes, for example, a wireless LAN function and wirelessly connects the wearable device 10 and an access point 112.

The motion sensor 154 is a sensor including a three-axis acceleration sensor, a three-axis gyroscope sensor and a three-axis geomagnetic sensor integrated with each other and is configured to detect movements of the head of the user of the wearable device 10 and determine the direction of the user's head base on the detection result. Note that the state of the operator may also be detected by the microphone 148, a barometer or the like. The state of the operator includes work content, work progress and the like in addition to a walking state and a resting state. By using movements detected by the motion sensor 154, a barometric altitude or the like, it is determined whether the feature quantities obtained from the detection result correspond to the feature quantities of each work step obtained from an operator or the like beforehand, and it is thereby determined which step in a plurality of work steps the operator is performing or has finished with. Further, it is also possible to determine which step in a plurality of work steps the operator is performing or has finished with by determining whether the feature quantities of environmental sounds input from the microphone 148 correspond to the feature quantities of environmental sounds unique to each work step obtained beforehand.

The sight line detector 156 is provided in the center on the inner side of the frame of the eyeglasses and directed to the user's face, and is configured to capture an image of the eyeballs of the user and detect a line of vision. Further, it is also possible to configure the sight line detector 156 to detect the irises of the user. The gesture sensor 158 is a sensor configured to determine a gesture such as movements of the fingers. More specifically, the gesture sensor 158 is a sensor configured to determine the user's gesture by analyzing movements of the fingers made on the touchpad 55 provided in the projector 12 or movements of the hands or the fingers shown in an image captured by the camera 59. The vibrator 68 is configured to vibrate the temple of the wearable device 10 by vibrating the projector 12 and communicate certain information to the user. The position data receiver 159 is configured to receive beacons including position data transmitted from a plurality of the position data transmitters 113 installed in the area of the LAN 102 using a short-range wireless communication such as RF-ID. In the case of a short-range wireless communication, the position of the transmitter and the position of the receiver (wearable device) can be estimated to be substantially the same as each other. The GPS unit 155 is configured to detect the position (x, y, z) of the wearable device 10. By generalizing this result, the detection result of the position data receiver 159 and the detection result of the photo detector 62 of FIG. 3, the position of the user and the shift of the position can be detected more accurately.

The display 30 is configured to display an instruction or an incoming call from the supervisor's device 104 or the data management server 116, the work state of an operator detected by the motion sensor 154 and the like. The display image is displayed on the screen 16 by the projection processor 150.

It is possible to take an incoming call by using the microphone 148 and the speaker 54.

The supervisor's device 104 may have a structure the same as that of the wearable device 10 or may have a structure the same as that of an ordinary personal computer or tablet computer. The electrical configuration of an ordinary personal computer or tablet computer is equivalent to the electrical configuration of the wearable device 10 except that the projection processor 150, the camera 59, the motion sensor 154, the sight line detector 156, the gesture sensor 158 and the like are omitted. The position of the supervisor's device 104 is detected by the GPS.

With reference to FIGS. 8A and 8B, an example of the apparatus state sensor 108 attached to the manufacturing apparatus 106 will be described below. FIG. 8A shows attachment positions to the apparatus, while FIG. 8B shows the structure of the sensor 108. Conventionally, each time a problem occurs in a manufacturing apparatus, an operator checks the portion in the manufacturing apparatus having a problem and repairs the apparatus, and investigates the cause of the problem. Therefore, the maintenance time of the manufacturing apparatus (operation suspension time of the manufacturing apparatus) increases and this leads to a decrease in the productivity. In the present embodiment, the data management server 116 automatically detects or recognizes the portion in the manufacturing apparatus having a problem by collecting and integrating the apparatus state data obtained from the apparatus state sensor 108 connected to the network 102. As a result, since the portion in the manufacturing apparatus having a problem can be automatically diagnosed, it is possible to significantly decrease the maintenance time of the manufacturing apparatus (operation suspension time of the manufacturing apparatus) and thereby prevent a decrease in the productivity.

The apparatus state sensor 108 includes an acceleration sensor 108a and a wireless communication device 108b and is configured to transmit an acceleration signal detected by the acceleration sensor 108a to the data management server 116 via the wireless communication device 108b and the network 102. The apparatus state sensor 108 is provided with an attachment portion or a fixing portion so that the apparatus state sensor 108 can be easily attached to an existing manufacturing apparatus. An adhesive layer may be formed on the attachment portion in advance or an adhesive agent may be applied thereto at the time of attachment. Alternatively, the apparatus state sensor 108 may be attached to an existing manufacturing apparatus by screwing the fixing portion into the manufacturing apparatus.

To realize the automatic diagnosis of a portion in a manufacturing apparatus having a problem, it is necessary to automatically collect the operation state data of each unit of a manufacturing apparatus. In the case of achieving the automatic diagnosis by buying or replacing with a new manufacturing apparatus, the cost increases significantly. However, in the present embodiment, it is possible to realize the automatic diagnosis by simply attaching a sensor available at a significantly low cost to each unit of an existing manufacturing apparatus. Therefore, it is possible to add the environment of the automatic problem diagnosis inexpensively while maintaining the environment of an existing apparatus.

As shown in FIG. 8A, the apparatus state sensor 108 is fixed, for example, to a part of a moving belt 136, a movable arm 124 configured to hold products or a part of a movable shaft 132. Then, if a portion which moves in a normal operation stands still, it is determined that the movable portion has a problem.

The controller 118 in the data management server 116 stores handbooks for repairing, maintaining and checking the respective portions of various manufacturing apparatuses, namely, maintenance procedure handbooks in advance, and makes an appropriate work checklist based on a result of the above-described automatic diagnosis.

In FIGS. 8A and 8B, as an example of the apparatus state sensor 108, an acceleration detection method has been described. However, the above-described method is in no way restrictive, and various physical quantities or chemical quantities such as a temperature or a conducting current value may also be used. Further, it is also possible to perform the automatic diagnosis of the portion in the manufacturing apparatus having a problem by comparing images captured by a camera or environmental sounds collected by a microphone.

If a manufacturing apparatus having a problem is detected by the method described above with reference to FIGS. 8A and 8B, the data management server 116 automatically selects an operator who is to perform maintenance of the manufacturing apparatus and displays maintenance procedure or a work checklist derived from the maintenance procedure on the wearable device 10 of the operator. The data management server 116 selects an operator, for example, (i) who is near the manufacturing apparatus having a problem, (ii) who can stop the work the operator is currently engaging with and (iii) who can perform the maintenance work. In this way, it is possible to minimize a time loss in dispatching an operator to the manufacturing device having a problem.

Figure 9:
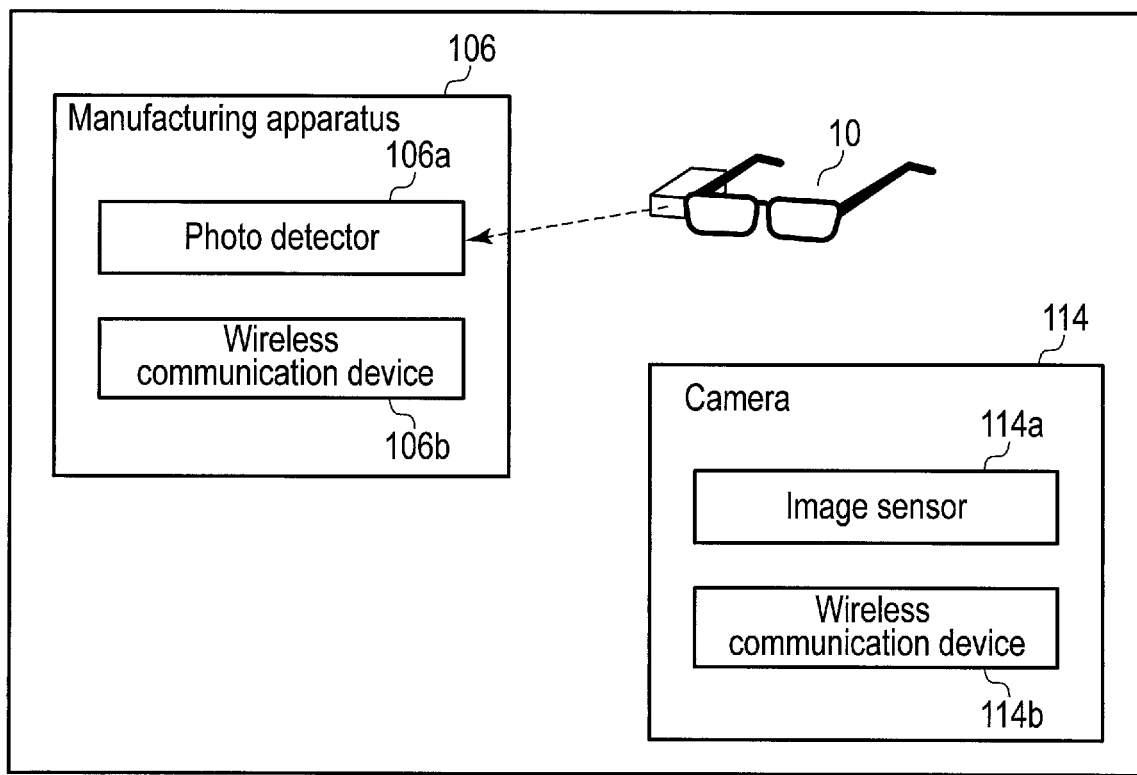
FIG. 9 shows an example of a sensor for detecting movements of a user.
Figures 13A, 13B:
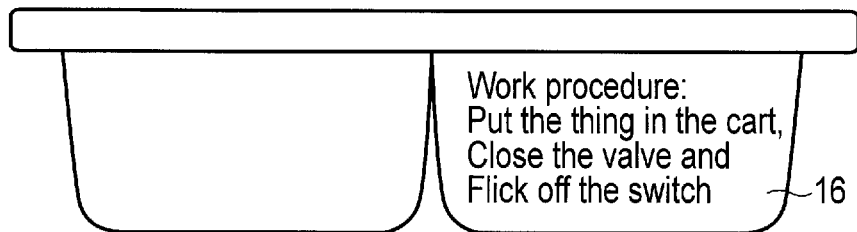
FIG. 13A shows an example of a workflow displayed by the system.
FIG. 13B shows an example of a work record made by the system.

As a method of most efficiently searching an operator near the manufacturing apparatus having a problem, in the present embodiment, a photo detector 106a similar to the photo detector 62 of FIG. 4 and a wireless communication device 106b are attached to a part of the manufacturing apparatus 106 as shown in FIG. 9. As described above with reference to FIGS. 5A-5K, the leaking light 50 radiating from the wearable device 10 includes the device ID data of the device 10. Therefore, if the data included in the leaking light 50 is detected by the photo detector 106a and transmitted to the data management server 116 via the wireless communication device 106b and the network 102, the data management server 116 can recognize the wearable devices 10, that is, the operators near the manufacturing apparatus having a problem. The data management server 116 selects an operator who is to perform maintenance of the target manufacturing apparatus based on the data and transmits a work checklist to the wearable device 10 of the operator. As shown in FIG. 13A, the work checklist is displayed on the screen 16 of the device 10. Note that, although the work checklist is simplified in FIG. 13A for the sake of convenience, the actual work checklist is as follows.

Put the thing in the cart.
Close the valve.
Flick off the on/off switch.
Flick off the first light switch.
Flick off the second light switch.

As described above, since the leaking light 50 radiating from the wearable device 10 is detected, collected and summarized in real time, it is possible to identify an operator near the manufacturing apparatus 106 subjected to maintenance easily and accurately. Consequently, it becomes possible to save the time of dispatching an operator to the apparatus and reduce the maintenance time, and thereby prevent a decrease in the manufacturing efficiency.

Note that, as another method of recognizing operators near the target manufacturing apparatus, there is a method of using the camera 114 provided near the manufacturing apparatus 106. An image sensor 114a in the camera 114 captures an image around the manufacturing apparatus 106 and transmits the image data to the data management server 116 via a wireless communication 114b. The data management server 116 analyzes the received image data and automatically identifies operators therein.

Figure 10A:
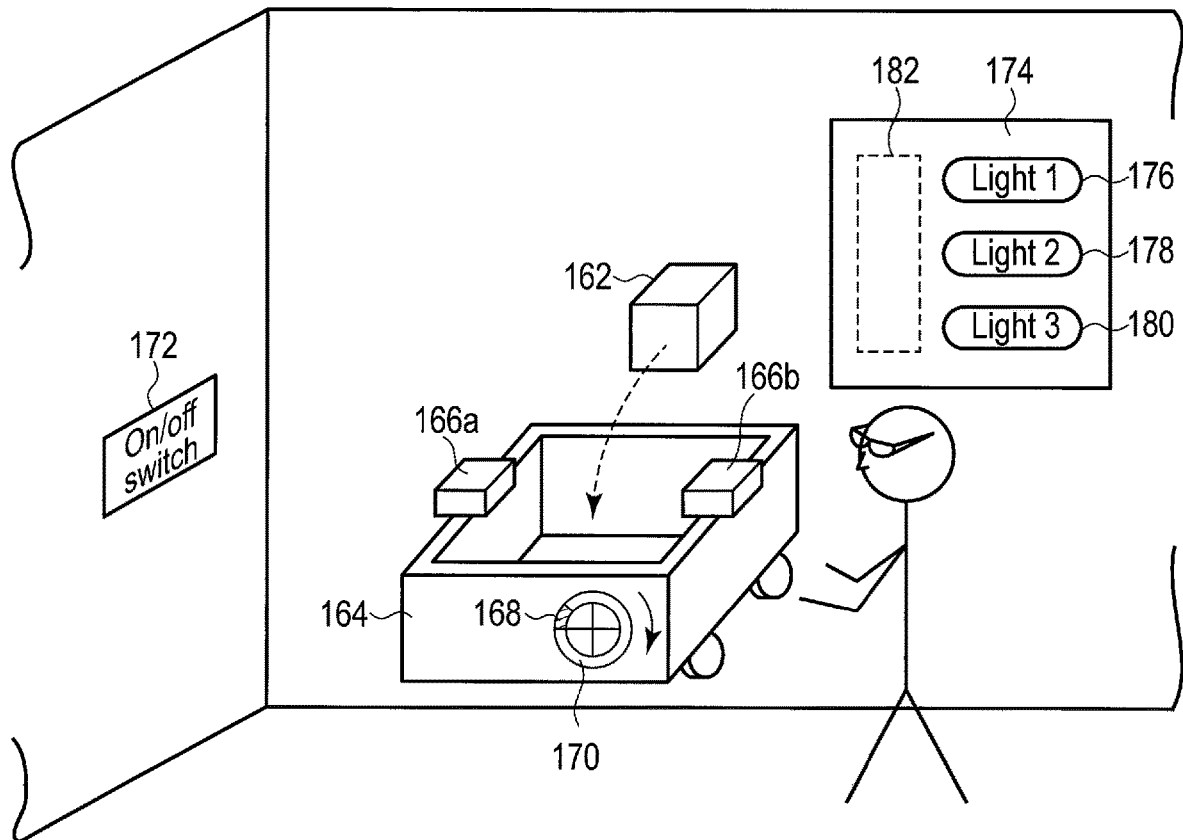
FIGS. 10A and 10B show an example of a usage environment of the system.
Figure 10B:
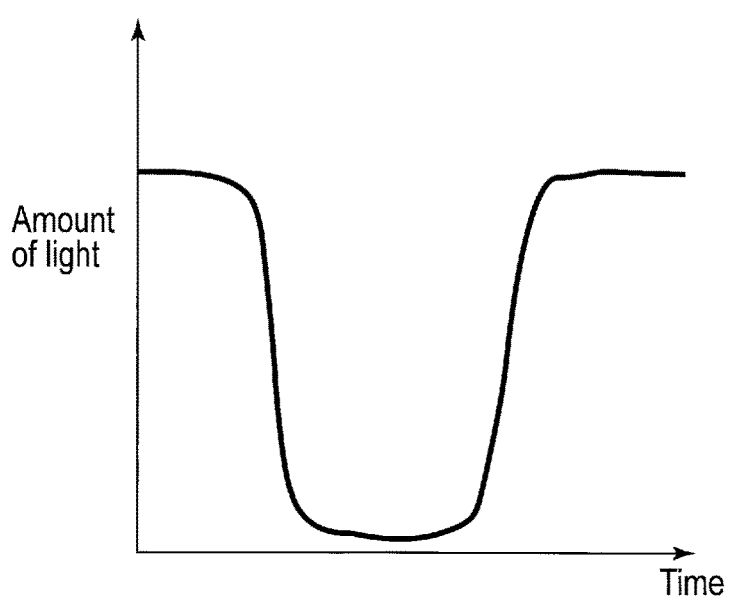

With reference to FIGS. 10A and 10B, an example of a case where an operator performs work in accordance with a work checklist will be described. If a work checklist of FIG. 13A is displayed on the screen 16, an operator starts work. Here, if the whole checklist is displayed at a time, there are some cases where the letters in the checklist become too small to see. In that case, only first or first few steps may be displayed by larger letters, and then the checklist may be updated as each step ends by automatically recognizing the progress of work step by step. The operator in the operation site of FIG. 10A puts a thing 162 in a cart 164, closes a valve 170 (or turns a handle 170 to a specified angle), flicks off an on/off switch 172, flick off a first light switch 176 and a third light switch 180 according to the work checklist. In the present embodiment, the movements of the operator are automatically recognized and identified in real time by the user movement sensor 110 attached to the manufacturing apparatus 106 and the work completion times are automatically written in the work checklist (see FIG. 13B). If the last work step ends, a work report is automatically made in the data management server 116, and the contents are displayed on the supervisor's device 104. The work checklist (FIG. 13B) corresponds to the work checklist (FIG. 13A) containing the completion times input thereto.

As a method of automatic recognition and identification of user's movements by the user movement sensor 110, various detection techniques and the combinations thereof may be used. For example, it is possible to perform automatic recognition and identification of user's movements by using the camera 114 or 59 and analyzing an image of the user's movements. Note that, in the method of analyzing an image of the user's movements captured by the camera 114, depending on the situation, the user's movements may be hidden behind in the image. Alternatively, it is possible to use a sound recognition technique. If it is determined in advance that the operator produces a specific sound as the operator finishes with the work of each item of the work checklist (maintenance work procedure) displayed on the wearable device 10, it is possible to perform automatic recognition and identification of the user's movements by detecting an input of the specific sound with the microphone 148. Alternatively, it is also possible to perform automatic recognition and identification of the user's movements by detecting environmental sounds produced in specific work using the microphone 148 or a built-in microphone of the apparatus state sensor 108. Further, there is a method of identifying a predetermined operator's gesture and thereby performing automatic recognition and identification of operator's movements. As a method of identifying an operator's gesture, images of operator's movements captured by the cameras 59 and 114 may be analyzed or detection results of the leaking light 50 of the wearable devices 10 by a plurality of the photo detectors 62 or the photo detectors 106a attached to the manufacturing apparatuses 106 may be compared with each other.

A pair of a light emitting device 166a and a photo detector 166b is provided in an opening portion of the cart 164, and it is automatically detected that the thing 162 is put in or taken out of the cart 164 by detecting the interception of light caused if the thing 162 passes through the opening portion of the cart 164. FIG. 10B shows the signal characteristics detected by the photo detector 166b if the thing 162 is put in or taken out of the cart 164. The vertical axis shows the amount of light detected by the photo detector 166b while the horizontal axis shows the time passed. If the thing 162 passes through the opening portion of the cart 164, the amount of light the photo detector 166b detects decreases. As a method of detecting that the thing 162 is put in or taken out of the cart 164, not the above-described method using light but various other methods may be used.

An example of the detection method which realizes the real-time automatic recognition and identification of movements other than the putting in or taking out of the thing such as the closing the valve, the flicking off the on/off switch and the flicking off the light switch will be described below. In general, to perform maintenance (maintenance, checkups and repairs) of the manufacturing apparatus, the operator needs to directly contact a predetermined portion in the manufacturing apparatus. By using this feature, in the present embodiment, if it is detected that the operator contacts a predetermined portion in the manufacturing apparatus, the detection result is reflected in the automatic recognition and identification of the operator's movements. According to this method, it is possible to perform detection easily and perform automatic recognition and identification with high accuracy. In the case of FIG. 10A, a contact sensor 168 is attached to the valve 170, and transparent contact sensors are attached respectively to the on/off switch 172 and a light switch board 174. The light switch board 174 includes the first, second and third light switches 176, 178 and 180.

The contact sensor as an example of the user movement sensor 110 includes a wireless communication function (for example, a short-range wireless communication) and a detection function of detecting the contact state of the operator. In the detection of the contact state, various elements configured to perform contact detection such as a piezoelectric element, a photo interrupter and an acceleration sensor (gyroscope sensor) can be used. The contact sensor of this type is attachable to existing facilities such as existing manufacturing apparatuses and is available at an extremely low cost. Therefore, it is possible to add a short-range wireless communication network environment inexpensively by simply attaching the contact sensor (user movement sensor 110) to an existing manufacturing apparatus while maintaining the existing infrastructure.

An example of the user movement sensor 100 is shown in FIGS. 11 and 12. FIG. 11 shows the user movement sensor 110 attached to an existing infrastructure, namely, the on/off switch 172 or the user movement sensor 110 (contact sensor 168) attached to the valve 170, while FIG. 12 shows the user movement sensor 110 attached to an existing infrastructure, namely, the light switch board 174.

As shown in FIG. 11, the user movement sensor 110 includes an adhesive layer 202 at the bottom, and further includes a control and communication circuit 204 and a solar cell 206 formed in this order on the adhesive layer 202. On the solar cell 206, a transparent conductive layer 208, a transparent intermediate layer 210, a transparent conductive layer 212 and a transparent uneven layer 214 are stacked one after another. The control and communication circuit 204 includes a function of performing wireless communication (short-range wireless communication) and a function of detecting contact with the operator. The circuit 204 is driven by the solar cell 206 to perform these functions. In the case of using a battery as a power supply, there is the trouble of battery replacement. Further, in the case of using an external power supply connected to a cable as a power supply, the cable blocks the operator from contacting. However, in the case of the solar cell 206, it is possible to drive the user movement sensor 110 for a long period of time without giving the trouble of battery replacement or obstructing the operator from contacting.

By stacking the control and communication circuit 204 configured to perform a short-range wireless communication and execute control below the solar cell 206, it is possible to increase the power generation efficiency of the solar cell 206 and reduce the plane size of the user movement sensor 110.

To use the solar cell 206, the solar cell 206 needs to be irradiated with surrounding light. Meanwhile, it is preferable that the portion configured to detect the user's contact is provided on the surface of the user movement sensor 110. As a method of satisfying both demands at the same time, a capacitance type detection method is adopted and the contact detection portion is made transparent. To detect the operator's contact or pressure by using a change in capacitance, the following structure is adopted: the transparent intermediate layer 210 formed of a transparent and elastic material (for example, a transparent organic material sheet) is sandwiched between the two transparent conductive layers 208 and 212 (for example, transparent organic material sheets). By applying an alternating-current voltage 216 between the two transparent conductive layers 208 and 212, the transparent conductive layers 208 and 212 are resonated with each other. If the operator contacts the surface of the user movement sensor 110, a change occurs in the capacitance, and consequently a change occurs in the above-described AC resonance state. By detecting a change in the AC resonance state, the operator's contact is detected. Note that this capacitance type detection method may not necessarily be used but any element may be used as long as the element allows at least a part of surrounding light to reach the solar cell 206 in the user movement sensor 110 and is configured to detect contact or pressure.

The transparent layer on the surface of the user movement sensor 110 is, for example, provided with small asperities. This functions as a non-slip surface, but it is possible to record information in Braille using the asperities for the sake of people with impaired vision.

As a method of fixing the user movement sensor 110 to a part of an existing manufacturing apparatus, although various fixing methods such as screwing may be adopted, it is possible to save space by directly bonding or attaching the sensor 110 thereto. As the bonding or attaching method, not only a method of directly bonding with an adhesive agent but also a method of using an adhesive sheet or an adhesive tape may be used. The adhesive layer 202 having characteristics of a double-faced adhesive tape may be used for the on/off switch 172 and the light switch board 174, and on the other hand, the adhesive layer 202 formed of a transparent adhesive layer may be used for the valve 170.

FIG. 12 shows the user movement sensor 110 attached to the light switch board 174. In the light switch board 174, since letters such as light 1, light 2 and light 3 are written on the surfaces of the first, second and third light switches 176, 178 and 180, it is preferable that these letters be seen directly even if the user movement sensor 110 is attached. Therefore, the layers provided above the light switches 176, 178 and 180 preferably be transparent. Further, it is necessary to detect the contact states of the plurality of light switches 176, 178 and 180, respectively. Meanwhile, in the light switch board 174, there is a space 182 left in a portion not provided with the light switches 176, 178 and 180. To conform to such a situation, the user movement sensor 110 of FIG. 12 includes the transparent sheet 208, the transparent intermediate layer 210, the transparent sheet 212 and the transparent uneven layer 214 stacked in series on the adhesive layer 202. The transparent sheets 208 and 212 correspond to the transparent conductive layers 208 and 212 of FIG. 11, and the transparent sheet 208 includes three transparent conductive regions 208a, 208b and 208c and the transparent sheet 212 includes three transparent conductive regions 212a, 212b and 212c. The transparent conductive regions 208a and 212a are provided in the positions corresponding to the first light switch 176, the transparent conductive regions 208b and 212b are provided in the positions corresponding to the second light switch 178, and the transparent conductive regions 208c and 212c are provided in the positions corresponding to the third light switch 180. The AC voltage 216 is applied between the transparent sheets 208 and 212. By dividing the transparent sheet into three regions corresponding to the three light switches, it is possible to detect the contact states of the three light switches, respectively. Braille information may also be formed on the surface of the transparent uneven layer 214.

In a portion on the transparent uneven layer 214 corresponding to the left space 182 not provided with the light switches, a control circuit 204a and a communication circuit 204b are formed, and the solar cell 206 is formed thereon. Since the solar cell 206 is provided on the top, the power generation efficiency is high. Further, since the control circuit 204a, the communication circuit 204b and the solar cell 206 are located in the vertical direction, the plane size of the user movement sensor 110 is reduced.

According to the embodiment, by detecting the states of wearable devices and manufacturing apparatuses and displaying, based on the detection result, a workflow on the wearable device of an operator who is near a manufacturing apparatus requiring maintenance, checkups and repairs and who can perform the maintenance work, it is possible to provide the operator with useful information. Further, since completion of each step of the work is determined and a work report recording the progress of the work is made automatically based on the detection result of the states of the wearable device and the manufacturing apparatus, it is possible to save the operator the troubles thereof. Note that, since the detection of completion of work is realized simply by attaching a contact sensor to a manufacturing apparatus, it is possible to detect and recognize movements of the operator quite easily, inexpensively and accurately without making modifications to an existing manufacturing apparatus.

The present embodiment describes the case of performing maintenance of a manufacturing apparatus. However, the present embodiment is not necessarily limited to this case but may be applied to a case of monitoring user's movements corresponding to other purposes and displaying work contents according to the purposes. Further, the present embodiment describes providing a contact sensor for monitoring the user's movements in a portion which the user is likely to contact, but other sensors may be used instead.

Although the present embodiment describes the case of an eyeglasses-type wearable device, the present embodiment is also applicable to head-mounted type wearable devices of other types such as goggles and helmet types as well as to a wristband-type wearable device, a pendant-type wearable device and the like. For example, in the case of a helmet or goggles-type wearable device, since the projector 12 and the camera 59 can be attached to the helmet or the goggles, people with eye glasses can also use the wearable device. Further, in the case of a helmet-type wearable device, since the speaker 54 can be attached to the inner side of the helmet, the user can hear a sound clearly, and since a microphone can be attached to the helmet and the position of the microphone can be adjusted, the sound collection performance of the microphone improves.

As the sensors configured to detect the states of a wearable device and a manufacturing apparatus, various other sensors may be used appropriately instead of the sensors described above.

The present embodiment is applicable to wearable devices other than head-mounted type wearable devices. The present embodiment is also applicable to portable and light electronic devices carried with the users at all times as notebook computers, tablet computers and smart phones.

As to the share of functions between the wearable device and the data management server, the above description is in no way restrictive, but instead, some of the above-described functions of the wearable device may be realized as those of the data management server or some of the above-described functions of the data management server may be realized as those of the wearable device.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A system comprising:
a first wearable device and a second wearable device; and
a server communicatively coupled to the first wearable device and the second wearable device, wherein
the first wearable device is configured to transmit a first device identification,
the second wearable device is configured to transmit a second device identification,
the server is configured to manage a first relation among the first device identification, a first user identification, and the first wearable device and a second relation among the second device identification, a second user identification, and the second wearable device,
the server is configured to receive the first device identification or the second device identification and the first user identification or the second user identification, identify the first wearable device or the second wearable device based on the first device identification or the second device identification, and identify a user of the first wearable device or the second wearable device based on the first user identification or the second user identification,
the server is configured to generate a first image associated with the first wearable device or a second image associated with the second wearable device,
the first image is different from the second image,
the server is configured to transmit the first image to the first wearable device or transmit the second image to the second wearable device,
the first wearable device is configured to be attached to a first display configured to display a first display image,
the second wearable device is configured to be attached to a second display configured to display a second display image,
the first wearable device comprises
a first optical component set comprising a first lens configured to form a first visual image at a position which is a distance away from the first user, the first visual image being formed from the first display image displayed by the first display; and
a first user operable member configured to set an adjustment value relating to a projection angle of the first visual image,
the second wearable device comprises
a second optical component set comprising a second lens configured to form a second visual image at a position which is a distance away from the second user, the second visual image being formed from the second display image displayed by the second display; and
a second user operable member configured to set an adjustment value relating to a projection angle of the second visual image,
a position of the first visual image is changed by adjusting the projection angle of the first visual image using the first user operable member so that the first visual image is displayed at a position according to at least one of a shape or a size of the head of the first user; and
a position of the second visual image is changed by adjusting the projection angle of the second visual image using the second user operable member so that the second visual image is displayed at a position according to at least one of a shape or a size of the head of the second user.

2. The system of claim 1, wherein
the first wearable device comprises a third user operable member configured to set an adjustment value relating to at least one of a color tone or a brightness of the first visual image, and
the second wearable device comprises a fourth user operable member configured to set an adjustment value relating to at least one of a color tone or a brightness of the second visual image.

3. A method for a system comprising a first wearable device and a second wearable device; and a server communicatively coupled to the server,
wherein
the first wearable device is configured to transmit a first device identification,
the second wearable device is configured to transmit a second device identification,
the server is configured to manage a first relation among the first device identification, a first user identification, and the first wearable device and a second relation among the second device identification, a second user identification, and the second wearable device,
the server is configured to receive the first device identification or the second device identification and the first user identification or the second user identification, identify the first wearable device or the second wearable device based on the first device identification or the second device identification, and identify a user of the first wearable device or the second wearable device based on the first user identification or the second user identification,
the first wearable device is configured to be attached to a first display configured to display a first display image,
the second wearable device is configured to be attached to a second display configured to display a second display image,
the first wearable device comprises
a first optical component set comprising a first lens configured to form a first visual image at a position which is a distance away from the first user, the first visual image being formed from the first display image displayed by the first display; and
a first user operable member configured to set a first adjustment value relating to a projection angle of the first visual image,
the second wearable device comprises
a second optical component set comprising a second lens configured to form a second visual image at a position which is a distance away from the second user, the second visual image being formed from the second display image displayed by the second display; and
a second user operable member configured to set a second adjustment value relating to a projection angle of the second visual image, the method comprising:

changing a position of the first visual image based on the first adjustment value so that the first visual image is displayed at a position according to at least one of a shape or a size of the head of the first user; and
changing a position of the second visual image based on the second adjustment value so that the second visual image is displayed at a position according to at least one of a shape or a size of the head of the second user.

4. The method of claim 3, further comprising:
changing at least one of a color tone or a brightness of the first visual image based on a third operable member in the first wearable device; and
changing at least one of a color tone or a brightness of the second visual image based on a fourth operable member in the second wearable device.

5. A system comprising:
a first wearable device configured to transmit a first device identification; and
a server communicatively coupled to the first wearable device, the server is configured to
(A) manage a first relation among the first device identification, a first user identification and the first wearable device,
(B) receive the first device identification and the first user identification,
(C) identify the first wearable device based on the first device identification,
(D) identify a user of the first wearable device based on the first user identification, and
(E) generate a first image associated with the first wearable device and transmit the first image to the first wearable device,
wherein the first wearable device, configured to be attached to a first display configured to display a first display image, comprises (i) a first optical component set comprising a first lens configured to form a first visual image at a position which is a distance away from the first user, the first visual image being formed from the first display image displayed by the first display, and (ii) a first user operable member configured to set an adjustment value relating to a projection angle of the first visual image,
wherein a position of the first visual image is changed by adjusting the projection angle of the first visual image using the first user operable member so that the first visual image is displayed at a position according to at least one of a shape or a size of the head of the first user.

* * * * *